US007233970B2

(12) United States Patent
North et al.

(10) Patent No.: US 7,233,970 B2
(45) Date of Patent: Jun. 19, 2007

(54) COMPUTATIONAL METHOD, SYSTEM, AND APPARATUS

(75) Inventors: Greg North, Austin, TX (US); Scott Haban, Austin, TX (US); Kyle Stein, Austin, TX (US)

(73) Assignee: Cipher Corporation Limited, Stoneham, MA (US)

( * ) Notice: Subject to any disclaimer, the term of this patent is extended or adjusted under 35 U.S.C. 154(b) by 972 days.

(21) Appl. No.: 10/078,252

(22) Filed: Feb. 16, 2002

(65) Prior Publication Data

US 2002/0191450 A1 Dec. 19, 2002

Related U.S. Application Data

(63) Continuation-in-part of application No. 10/068,295, filed on Feb. 5, 2005, and a continuation-in-part of application No. 10/068,294, filed on Feb. 5, 2002.

(60) Provisional application No. 60/300,955, filed on Jun. 26, 2001, provisional application No. 60/300,957, filed on Jun. 26, 2001, provisional application No. 60/288,015, filed on May 2, 2001, provisional application No. 60/326,266, filed on Oct. 1, 2001, provisional application No. 60/326,252, filed on Oct. 1, 2001, provisional application No. 60/326,251, filed on Oct. 1, 2001, provisional application No. 60/326,250, filed on Oct. 1, 2001.

(51) Int. Cl.
*G06F 7/38* (2006.01)
*H04K 1/00* (2006.01)

(52) U.S. Cl. .......................... 708/491; 380/28
(58) Field of Classification Search .............. 708/491, 708/492
See application file for complete search history.

(56) References Cited

U.S. PATENT DOCUMENTS 4,799,149 A    1/1989   Wolf (Continued)

FOREIGN PATENT DOCUMENTS

WO    WO 01/29652 A2 *   4/2001

OTHER PUBLICATIONS

Dimitrov, V. and Cooklev, T., "Two Algorithms for Modular Exponentiation Using Nonstandard Arithmetics" IEICE Trans. Fundamentals, vol. E78-A, No. 1, Jan. 1995.

(Continued)

*Primary Examiner*—Chuong D. Ngo
(74) *Attorney, Agent, or Firm*—John A. Fortkort; Fortkort & Houston P.C.

(57) ABSTRACT

A method, system, and apparatus for performing computations.

In a method, arguments X and K are loaded into session memory, and X mod P and X mod Q are computed to give, respectively, $X_P$ and $X_Q$. $X_P$ and $X_Q$ are exponentiated to compute, respectively, $C_P$ and $C_Q$. $C_P$ and $C_Q$ are merged to compute C, which is then retrieved from the session memory.

A system includes a computing device and at least one computational apparatus, wherein the computing device is configured to use the computational apparatus to perform accelerated computations.

An apparatus includes a chaining controller and a plurality of computational devices. A first chaining subset of the plurality of computational devices includes at least two of the plurality of computational devices, and the chaining controller is configured to instruct the first chaining subset to operate as a first computational chain.

42 Claims, 13 Drawing Sheets

U.S. PATENT DOCUMENTS

| | | | |
|---|---|---|---|
| 5,542,061 | A | 7/1996 | Omata |
| 5,699,537 | A | 12/1997 | Sharangpani et al. |
| 5,724,279 | A | 3/1998 | Benaloh et al. |
| 5,764,554 | A | 6/1998 | Monier |
| 5,983,299 | A | 11/1999 | Qureshi |
| 5,987,574 | A | 11/1999 | Paluch |
| 6,088,453 | A | 7/2000 | Shimbo |
| 6,134,244 | A | 10/2000 | Van Renesse et al. |
| 6,141,705 | A | 10/2000 | Anand et al. |
| 6,151,393 | A | 11/2000 | Jeong |
| 6,157,955 | A | 12/2000 | Narad et al. |
| 6,282,290 | B1 * | 8/2001 | Powell et al. ............ 380/28 |
| 6,341,299 | B1 | 1/2002 | Romain |
| 6,963,979 | B2 * | 11/2005 | Fairclough et al. ...... 713/189 |

OTHER PUBLICATIONS

Koc, C.K. and Hung, C.Y., "Carry-Save Adders for Computing the Product AB Modulo N" Electronics Letters, vol. 26, No. 13, (Jun. 21, 1990), pp. 899-900.

Freking, W.L. and Parhi, K.K., "Montgomery Modular Multiplication and Exponentiation in the Residue Number System" Proc. 33rd Asilomar Conf. Signals Systems and Computer, Oct. 1999, pp. 1312-1316.

Tenca, A.F. and Koc, C.K., "A Scalable Architecture for Montgomery Multiplication" in: Koc, C.K. and Paar, C., Cryptographic Hardware and Embedded Systems, CHES 99, Lecture Notes in Computer Science, No. 1717, 1998, New York, NY: Springer-Verlog, 1999.

Koc, C.K. and Acar, T., "Montgomery Multiplication in GF (2k)" 3rd Annual Workshop on Selected Areas in Cryptography, (Aug. 15-16, 1996), pp. 95-106.

Bajard, J.C., et al "An RNS Montgomery Modular Multiplication Algorithm" IEEE Transactions on Computer, vol. 47, No. 7, (Jul. 1998), pp. 766-776.

Eldridge, S.E., "A Faster Modular Multiplication Algorithm" International Journal of Computer Math, vol. 40, (1991), pp. 63-68.

Bossalaers, A.., et al "Comparison of Three Modular Reduction Functions" In Douglas R. Stinson, editor, Advances in Cryptology—CRYPTO '93, vol. 773 of Lecture Notes in Computer Science, (Aug. 22-26, 1993), pp. 166-174.

Montgomery, P.L., "Modular Multiplication Without Trial Division" Mathematics of Computation, vol. 44, No. 170 (Apr. 1985), pp. 519-521.

Koc, C.K., et al "Analyzing and Comparing Montgomery Multiplication Algorithms" IEEE Micro, vol. 16, Issue 3, (Jun. 1996), pp. 26-33.

Kornerup, P., "High-Radix Modular Multiplication for Cryptosystems" Department of Mathematics and Computer Science, (1993), pp. 277-283.

Sunar, B. and Koc, C.K., "An Efficient Optimal Normal Basis Type II Multiplier" Brief Contributions, IEEE Transactions on Computers, vol. 50, No. 1, (Jan. 2001), pp. 83-87.

Koc, C.K., "Comments on' Residue Arithmetic VLSI Array Architecture for Manipulator Pseudo-Inverse Jacobian Computation'" Communications, IEEE Transactions on Robotics and Automation, vol. 7, No. 5, (Oct. 1991), pp. 715-716.

Savas, E. and Koc, C.K., "The Montgomery Modular Inverse-Revisited" IEEE Transactions on Computers, vol. 49, No. 7, (Jul. 2000), pp. 763-766.

Walter, C.D., "Montgomery's Multiplication Technique: How to Make it Smaller and Faster" in Cryptographic Hardware and Embedded Systems—CHAS 1999, C. Paar (Eds.). K. Ko, Ed. 1999, Springer, Berlin Germany, pp. 61-72.

Blum, T., "Modular Exponentiation on Reconfigurable Hardware" Master's thesis, ECE Department, Worcester Polytechnic Institute, Submitted to Faculty Apr. 8, 1999, Published May 1999. Retrieved from the Internet <URL:http://www.wpi.edu/pubs/ETD/Available/etd-090399-090413/unrestricted/blum.pdf>.

Marwedel, P., et al. "Built in Chaining: Introducing Complex Components into Architectural Synthesis." Apr. 1996. Proceedings of the ASP-DAC, 1997. [online]. Retrieved from the Internet <URL:http://eldorado.uni-dortmund.de:8080/FB4/ls12/forshung/1997/aspdac/aspacPDF>.

Tiountchik, A., and Trichina, E., "RSA Acceleration with Field Programmable Gate Arrays" Lecture Notes in Computer Science, vol. 1587, pp. 164-176. Retrieved from the Internet: <URL:http://citeseer.nj.nec.com/274658.html>.

Menezes, A.J., et al "Handbook of Applied Cryptography" Boca Raton, CRC Press, 1997, pp. 591-607.

* cited by examiner

COMPUTATIONAL METHOD, SYSTEM, AND APPARATUS

CROSS-REFERENCE TO RELATED APPLICATIONS

This application claims the benefit of the following U.S. Provisional Applications, all of which are hereby incorporated by reference, and the content of which are not necessarily identical to the content of this application:

COMMONLY OWNED AND PREVIOUSLY FILED U.S. PROVISIONAL PATENT APPLICATIONS

| Atty. Dkt. # | Ser. No. | Title | Filing Date |
| --- | --- | --- | --- |
| 501143.000005 | 60/288,015 | Method and Apparatus for Shotgun Multiplication and Exponentiation | May 2, 2001 |
| 501143.000010 | 60/300,957 | Method and Residue Calculation Using Casting Out | June 26, 2001 |
| 501143.000011 | 60/300,955 | Add-Drop Layer 3 Ethernet Ring Switch | June 26, 2001 |
| 501431.000014 | 60/326,266 | Application Specific Information Processing System | October 1, 2001 |
| 501143.000015 | 60/326,252 | Efficient Use of DRAM-Based Devices For Small Discontiguous Memory Accesses | October 1, 2001 |
| 501143.000016 | 60/326,251 | Exponentiation Engine | October 1, 2001 |
| 501143.000017 | 60/326,250 | Method for Squaring | October 1, 2001 |

The current application shares some specification and figures with the following commonly owned and concurrently filed application, which is hereby incorporated by reference:

COMMONLY OWNED AND CONCURRENTLY FILED U.S. NONPROVISIONAL PATENT APPLICATIONS

| Atty. Dkt. # | Ser. No. | Title | Filing Date |
| --- | --- | --- | --- |
| 501143.000021 | 10/078,253 | Controller Architecture and Strategy For Small Discontiguous Accesses to High-Density Memory Devices | Feb. 16, 2002 |

Application Ser. No. 10/078,253 is now U.S. Pat. No. 6,738,874.

The current application is a continuation-in-part of the following commonly owned and previously filed applications, all of which are hereby incorporated by reference, and the benefit of 35 U.S.C. § 120 is claimed for these applications:

COMMONLY OWNED AND PREVIOUSLY FILED U.S. NONPROVISIONAL PATENT APPLICATIONS

| Atty. Dkt. # | Ser. No. | Title | Filing Date |
| --- | --- | --- | --- |
| 501143.000008 | 10/068,294 | Ring Arithmetic Method, System, and Apparatus | February 5, 2002 |
| 501143.000019 | 10/068,295 | Application-Specific Information-Processing Method, System, and Apparatus | February 5, 2002 |

The contents of the applications referenced in the tables above are not necessarily identical to the contents of this application.

All references cited hereafter are incorporated by reference to the maximum extent allowable by law. To the extent a reference may not be fully incorporated herein, it is incorporated by reference by background purposes and indicative of the knowledge of one of ordinary skill in the art.

BACKGROUND OF THE INVENTION

1. Field of the Invention

The present invention relates generally to integrated circuits and in particular to integrated circuits for performing accelerated computations.

2. Description of Related Art

Intense computation can take considerable time and therefore be undesirably expensive. Many innovations have been introduced to improve the speed and efficiency of intense computational processes. But each innovation left problems unsolved. Some of those problems are solved by the present invention.

BRIEF SUMMARY OF THE INVENTION

The present invention encompasses a method, system, and apparatus for performing computations.

In a method, arguments X and K are loaded into session memory, and X mod P and X mod Q are computed to give, respectively, $X_P$ and $X_Q$. $X_P$ and $X_Q$ are exponentiated to compute, respectively, $C_P$ and $C_Q$. $C_P$ and $C_Q$ are merged to compute C, which is then retrieved from the session memory.

A system includes a computing device and at least one computational apparatus, wherein the computing device is configured to use the computational apparatus to perform accelerated computations.

An apparatus includes a chaining controller and a plurality of computational devices. A first chaining subset of the plurality of computational devices includes at least two of the plurality of computational devices, and the chaining controller is configured to instruct the first chaining subset to operate as a first computational chain.

BRIEF DESCRIPTION OF THE DRAWINGS

The following drawings form part of the present specification and are included to further demonstrate certain aspects of the present invention. The figures are not necessarily drawn to scale. The invention may be better understood by reference to one or more of these drawings in combination with the detailed description of specific embodiments presented herein.

DETAILED DESCRIPTION OF PREFERRED EMBODIMENTS

Figure 1:
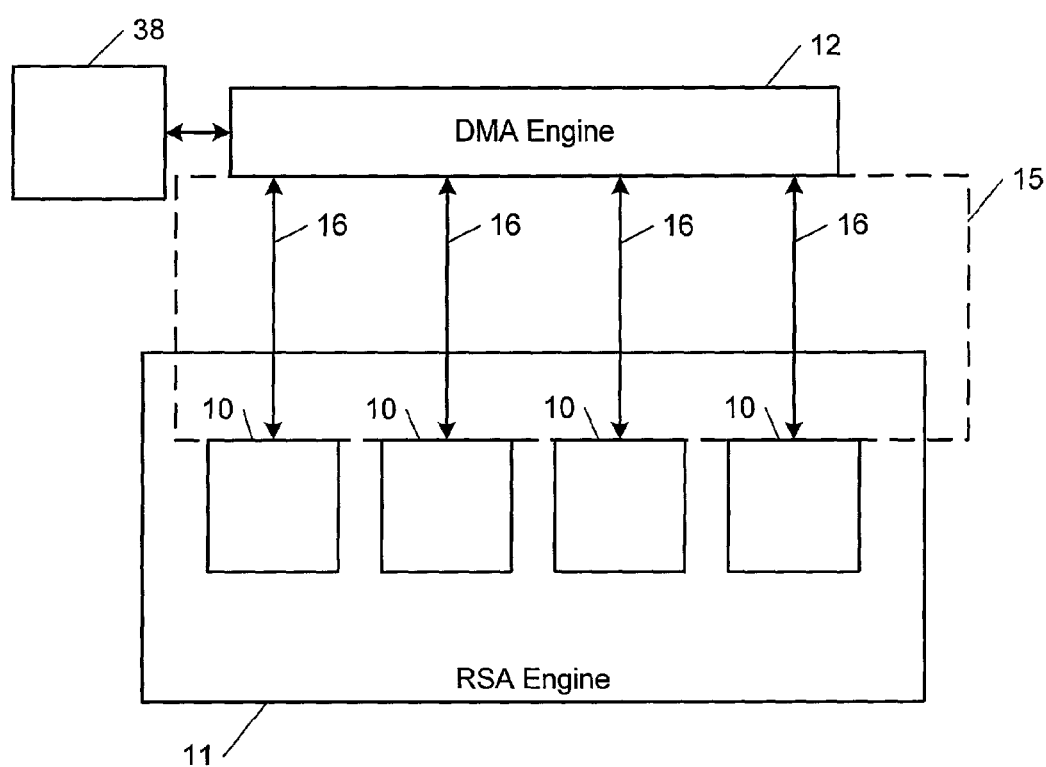
FIG. 1 shows an exponentiation system conceptual layout, in accordance with an embodiment of the present invention.

FIG. 1 shows an exponentiation system conceptual layout, in accordance with an embodiment of the present invention. This embodiment provides all of the hardware resources necessary to perform RSA exponentiation, which is required during the handshake at the start of an RSA session. The embodiment is composed of four instances of a base exponentiator called a computational device 10. Each computational device is capable of simultaneously processing eight 1K RSA exponentiations, four 2K exponentiations, or two 4K exponentiations. The computational devices 10 run on a clock that is independent from the rest of the chip, allowing their frequency to be adjusted for maximum performance.

The four computational devices 10 of this embodiment are carried on an RSA Engine 11, but operate independently from each other and are managed by a direct memory access (DMA) controller 12. The DMA controller 12 loads arguments and control information into a computational device's 10 internal memory and registers, and retrieves the exponentiation results from that computational device's 10 memory over a single burst-capable thirty-two-bit bus interface 15. This bus interface 15 is implemented as four independent connections 16 between the computational devices 10 and the DMA controller 12, although all storage within computational devices 10 maps into a single global address space. Other embodiments could obviously include appropriate interface alternatives without departing from the scope of the present invention.

Figure 2:
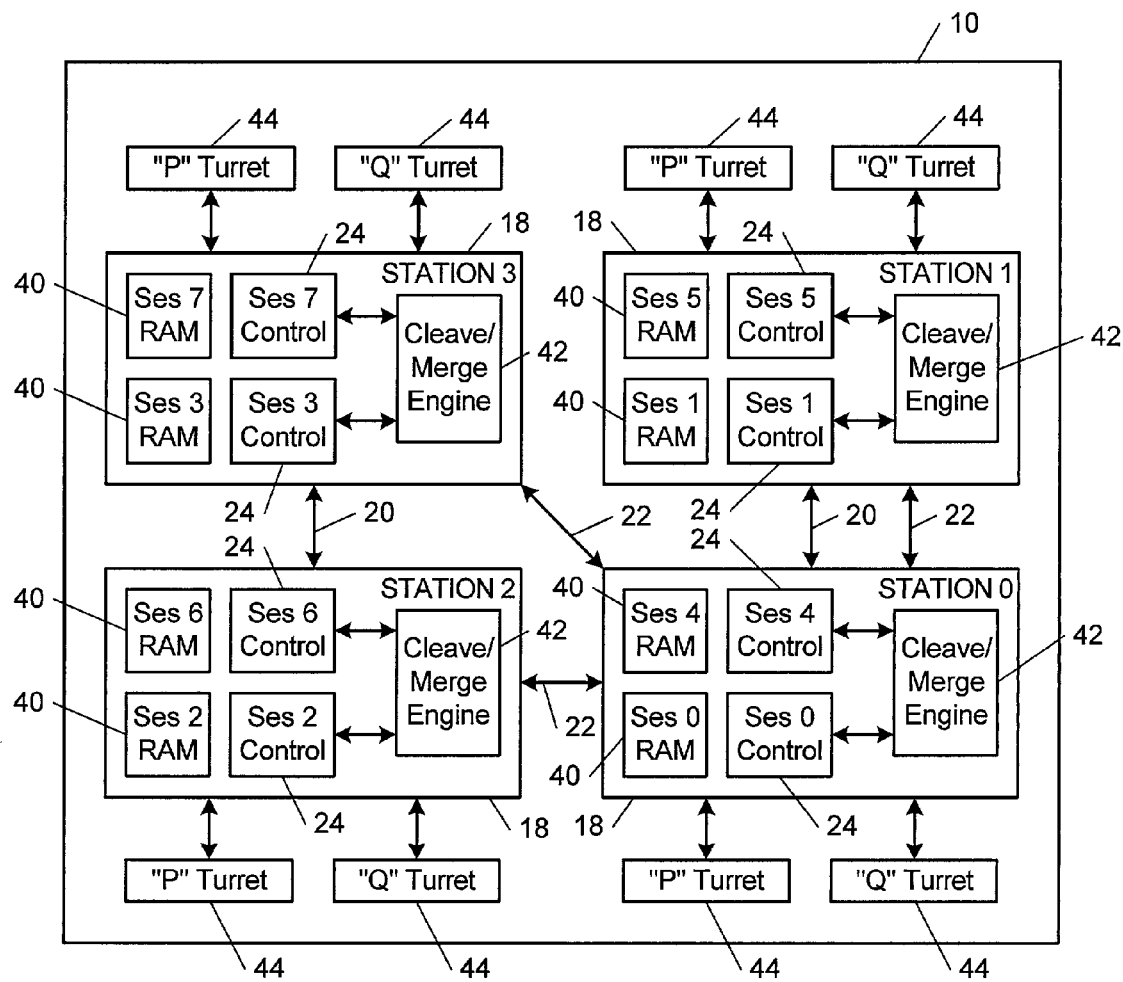
FIG. 2 shows a conceptual organization of a computational device having four stations, in accordance with an embodiment of the present invention.
Figure 3:
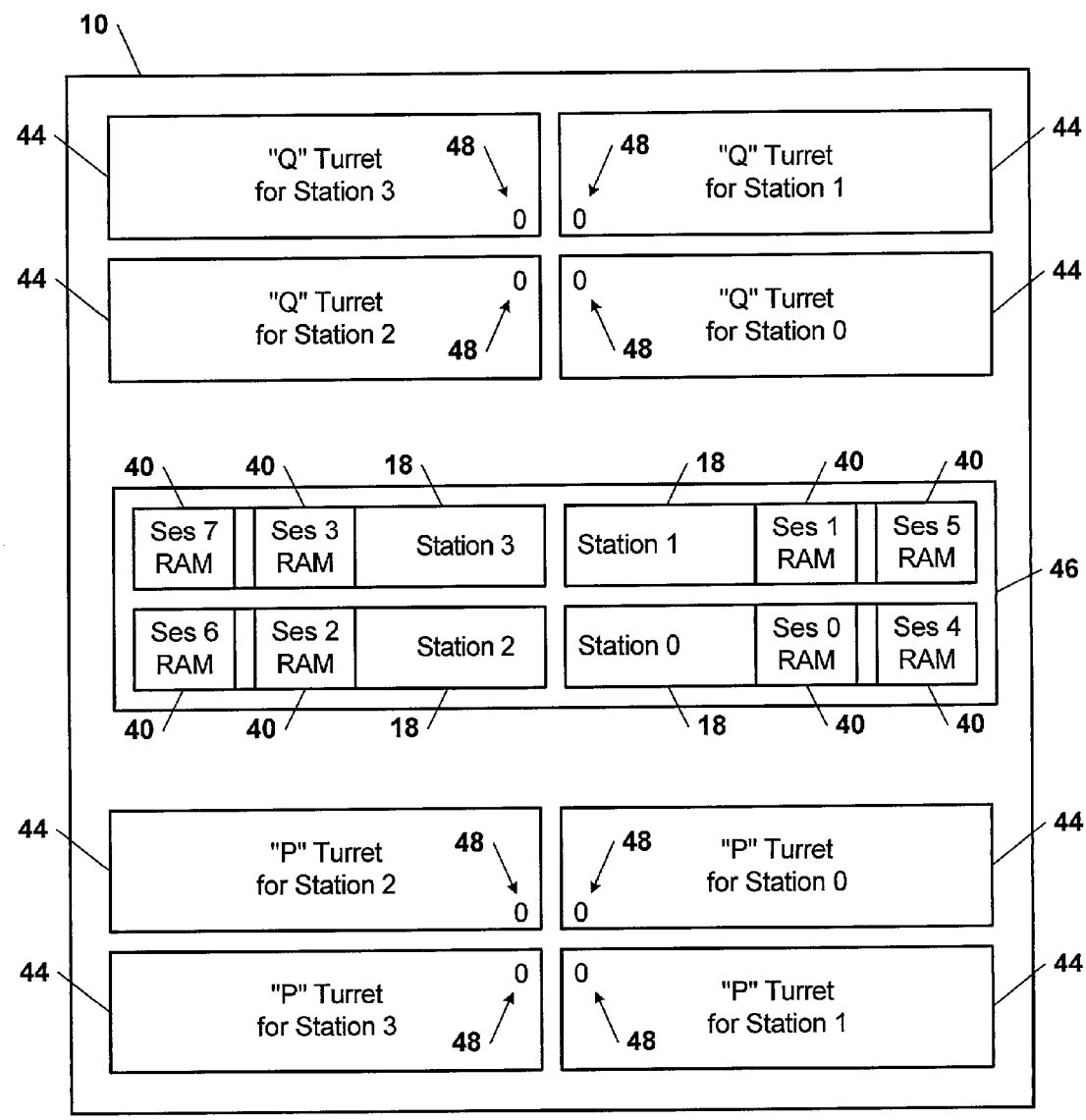
FIG. 3 shows a physical organization of a computational device having four stations, in accordance with an embodiment of the present invention.
Figure 4:
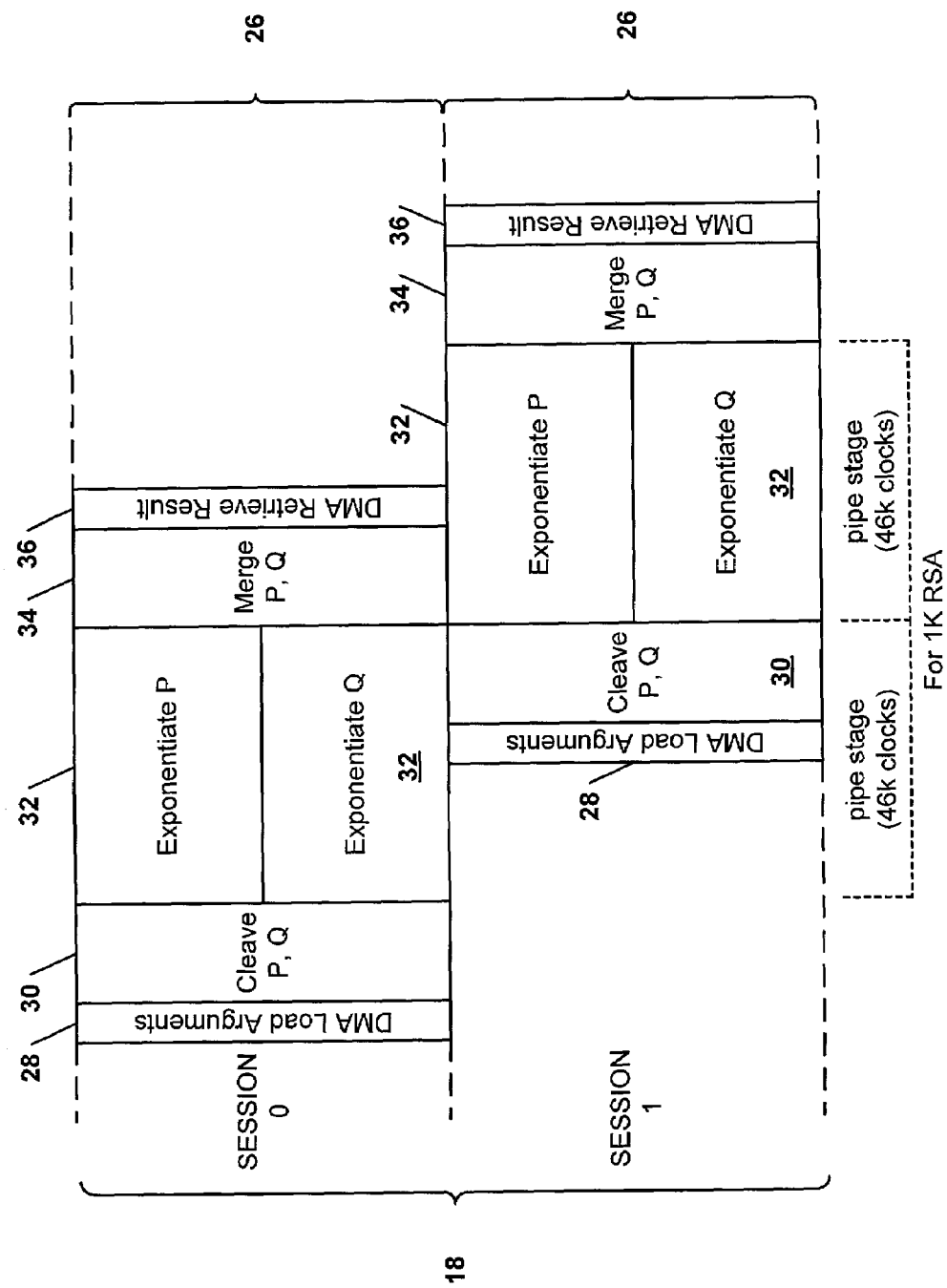
FIG. 4 shows a conceptualization of an exponentiation pipeline, in accordance with an embodiment of the present invention.

FIG. 2 shows a conceptual organization of a computational device 10 having four stations 18, in accordance with an embodiment of the present invention, and FIG. 3 shows a physical organization of a computational device 10 having four stations 18, in accordance with an embodiment of the present invention. The stations 18 operate independently when processing 1K RSA exponentiations, but are chained together 20 to process 2K exponentiations or chained together 22 to process 4K exponentiations. Each station 18 contains two session controllers 24, which can process separate RSA exponentiations concurrently. Both of the session controllers 24 within a station 18 have access to a single set of computation hardware for that station 18, so the hardware is shared between the two sessions 18 in a pipelined manner. FIG. 4 shows a conceptualization of an exponentiation pipeline 26, in accordance with an embodiment of the present invention. Because each session controller 24 can be working on an independent RSA exponentiation, we say that one computational device 10 can process up to eight exponentiations simultaneously (four stations× two sessions). With its four computational devices 10, the chip can process up to thirty-two exponentiations simultaneously.

Among other benefits, flexible chaining can avoid the waste of excess capacity faced by solutions that have only large-bit exponentiators, and also avoids wasted overhead due to iterating small-bit exponentiators to handle large-bit numbers as faced by non-chaining solutions that have only small-bit exponentiators.

Turning again to FIG. 4, an embodiment implements RSA exponentiation in five sequential steps: (1) Load session memory with arguments 28 (for example, encrypted data and certificate), (2) Cleave P 30, Cleave Q 30, (3) Exponentiate P 32, Exponentiate Q 32, (4) Merge P and Q 34, and (5) Retrieve result from session memory 36. Cleave, Exponentiate, and Merge are described below in greater detail.

Steps (1) and (5) are performed by the DMA controller 12. Arguments are read from a memory device 38, and delivered to one of eight internal session RAMs 40 within the computational device 10. At the end, the result is retrieved from the computational device 10 session RAM 40 by the DMA controller 12.

Steps (2) and (4) are performed by a single unit called the cleave/merge engine 42. The cleave process 30 takes a single 1024-bit data value (assuming 1K RSA) called X, and computes X mod P and X mod Q, producing two 512-bit results. The merge process 34 takes two 512-bit results from step (3), exponentiate 32, and uses them to produce a single 1024-bit value, which is the final result of the 1K RSA exponentiation. This embodiment uses a Chinese Remainder Theorem (CRT) cleave/merge to solve one 1024-bit exponentiation by solving two 512-bit exponentiations 32. Some embodiments do not use CRT.

Step (3) is performed by a pair of hardware exponentiators called turrets 44. Each computational device 10 contains a total of eight turrets 44—two for each station. Each turret 44 contains a very powerful hardware exponentiator including an iterative Montgomery multiplier which is capable of performing modulo exponentiation for a single 512-bit base, exponent, and modulo value. When a session reaches step 3, it uses a pair of turrets 44 to perform two 512-bit exponentiations in parallel (mod P and mod Q). The two 512-bit exponentiation results are later combined into a single 1024-bit result during the merge 34 step. For 2K or 4K RSA, it is necessary to chain two or four "P" turrets 44 together, and to similarly chain the "Q" turrets 44 together, allowing exponentiations of 1024-bit or 2048-bit values.

Returning to FIG. 2, the conceptual organization of a single computational device 10 is illustrated. Each of the four stations 18 contains a pair of session controllers 24, either of which can command that station's 18 cleave/merge engine 42, and a pair of turrets 44 (P and Q) dedicated to that station 18. Connections 20 and 22 between the stations 18 illustrate the chaining 20 of stations (0,1) and (2,3) for 2K RSA, and the chaining 22 of stations (0,1,2,3) for 4K RSA. For 2K and 4K RSA, only one session controller 24 is needed to control 2 or 4 stations 18. The controlling station 18 is called the base station, and the others are called satellite stations for this computation. For the 2K RSA of chain 20 between stations 0 and 1, station 0 is a base station, and station 1 is its satellite. Likewise, for the 2K RSA of chain 20 between stations 2 and 3, station 2 is a base station and station 3 is its satellite. For the 4K RSA of chain 22, station 0 is the base station, and stations 1, 2, and 3 are all satellites.

Returning to FIG. 3, the physical organization of the computational device 10 block of an embodiment on the chip is shown. The station/session controllers (not shown) and 192×32-bit session RAMs are contained within a control block 46. This block 46 is placed in the center of the computational device 10. The large, arrayed hardware which makes up the turrets 44 are placed above and below the soft control block 46, with all "P" turrets on one side and "Q" turrets on the other, to facilitate chaining of turrets 44 for 2K and 4K RSA. Furthermore, the four turrets 44 of each block are mirrored in both X and Y dimensions to place the least significant register bits 48 from each turret 44 near each other in the center of the block.

Revisiting FIG. 4, pipelines 26 are depicted. A computational device 10 contains four stations 18, each with a single cleave/merge engine 42 and a single P/Q turret pair. However, at any given time the computational device 10 can be processing up to eight concurrent RSA sessions, because each station 18 controls a two-stage pipeline 26 that allows two sessions to run concurrently. One session can work on Cleave 30 or Merge 34, while the other session uses a pair of turrets 44 to work on Exponentiate 32. With both sessions working on a different part of the RSA exponentiation process, all hardware will receive maximum utilization in a fully loaded system.

To facilitate this pipeline 26 schedule, the Cleave/Merge engine 42 was designed with just enough hardware parallelism to allow it to complete a cleave 30 or merge 34 in about half the number of cycles required for the exponentiate 32. If a 512-bit exponentiate (used in 1K RSA) requires about N clock cycles, then the total latency is about 2N cycles for the full RSA exponentiation. Thus, in a loaded system, sessions will be retired at twice the rate indicated by the latency, due to the two-session pipeline 26 that occurs in each station.

The RSA exponentiation input arguments are delivered by the DMA controller 12, coming from two sources. The data to be decrypted (X) is 1024 bits for 1K RSA, and is copied from the memory device 38 to one of the computational device 10 session RAMs 40, thirty-two bits at a time. The nine other inputs are 512 bits each, are precomputed external to the chip, and are copied from the memory device 38 to the computational device session RAM 40 when the computational device 10 begins processing a session. The following table shows the input arguments for 1K RSA:

| Symbol | Size | Description |
| --- | --- | --- |
| X | 1024 bits | Data to be decrypted |
| P | 512 bits | P modulus, a prime number. Note that P × Q = N, the RSA modulus |
| Q | 512 bits | Q modulus, a prime number |
| $D_P$ | 512 bits | exponent mod P, equals D mod (P − 1), where D is 1024-bit RSA private key |
| $D_Q$ | 512 bits | exponent mod Q, equals D mod (Q − 1), where D is 1024-bit RSA private key |
| $2^{\delta P}$ | 512 bits | "delta" value for P, used at end of exponentiation to fix Montgomery result |
| $2^{\delta Q}$ | 512 bits | "delta" value for Q, used at end of exponentiation to fix Montgomery result |
| μP | 512 bits | "mu" value for P, equals floor($2^{1024}$/P), used during cleave |
| μQ | 512 bits | "mu" value for Q, equals floor($2^{1024}$/Q), used during cleave |
| $P^{-1}$ | 512 bits | inverse of P, equals ($P^{-1}$ mod Q), used during merge |

All sizes in the above table double for 2K RSA, and quadruple for 4K RSA.

In an embodiment, the DMA controller 12 must load the required arguments into one or more session RAMs 40 before RSA exponentiation can begin. After the computation has finished, the result is retrieved from the same session RAMs 40.

In an embodiment, all registers and memory within the RSA Engine 11 are accessible in a single, continuous address space. During normal operation of this embodiment, only the DMA controller 12 will access the computational device 10 registers and memory. The DMA controller 12 will handle the initial configuration, loading of arguments, and retrieval of results.

This section describes the steps of an embodiment to run 1K, 2K and 4K RSA exponentiation. It assumes that a pair of thirty-two-bit registers exist in the DMA controller 12: one which indicates "busy" for each of the thirty-two available session controllers 24, and one which indicates "expired" for each of the thirty-two session controllers 24.

The following steps describe this embodiment's 1K RSA exponentiation:

Step 1: Find a single session controller 24 that is not busy, from the thirty-two available session controllers 24, by checking the state of the "busy" register in the DMA controller 12.

Step 2: DMA controller 12 sets the busy bit for the chosen session controller 24.

Step 3: DMA controller 12 transfers X data from the memory device 38 to the selected RSA session RAM 40.

Step 4: DMA controller 12 transfers the input arguments from the memory device 38 to the selected RSA session RAM 40.

Step 5: DMA controller 12 writes to the Session Control Register to indicate 1K RSA and starts the session running.

Step 6: When session has completed, the session controller 24 pulses the corresponding "done" signal to the DMA controller 12, to indicate the result is ready for retrieval.

Step 7: The DMA controller 12 transfers the result from the RSA session RAM 40.

Step 8: When result has transferred, the DMA controller 12 clears the busy bit for the chosen session controller 24.

The following steps describe this embodiment's 2K RSA exponentiation:

Step 1: Find two session controllers 24 that are not busy, from the thirty-two available session controllers 24, by checking the state of the "busy" register in the DMA controller 12. The chosen session controllers 24 must be an adjacent even, odd pair, so that they come from adjacent stations 18 as shown in FIG. 3. Legal pairings are: (session 0, session 1), (session 2, session 3), (session 4, session 5), or (session 6, session 7).

Step 2: DMA controller 12 sets the busy bits for both of the chosen session controllers 24.

Step 3: DMA controller 12 transfers X data from the memory device 38 to the computational device 10. The transfer is interleaved across the two session RAMs 40.

Step 4: DMA controller 12 transfers the input arguments from the memory device 38 to the computational device 10; i.e., to the session RAMs 40.

Step 5: DMA controller 12 configures the upper (satellite) station 18 for 2K RSA but does not start it running.

Step 6: DMA controller 12 configures the lower (base) station 18 for 2K RSA and starts the session running.

Step 7: When session has completed, the base station 18 session controller 24 simultaneously pulses both "done" signals to the DMA controller 12, corresponding to the two session controllers 24 used. This indicates the result is ready for retrieval.

Step 8: The DMA controller 12 transfers the result from both of the RSA session RAMs 40.

Step 9: When result has transferred, the DMA controller 12 clears the busy bits for both of the chosen session controllers 24.

The following steps describe this embodiment's 4K RSA exponentiation:

Step 1: Find four session controllers 24 which are not busy, from the thirty-two available session controllers 24, by checking the state of the "busy" register in the DMA controller 12. The chosen session controllers 24 must all reside within the same computational device 10, so there are only two possible groupings: (sessions 0,1,2,3) or (sessions 4,5,6,7).

Step 2: DMA controller 12 sets the busy bits for all four of the chosen session controllers 24.

Step 3: DMA controller 12 transfers X data from the memory device 38 to the computational device 10. The transfer is interleaved across the four session RAMs 40.

Step 4: DMA controller 12 transfers the input arguments from the memory device 38 to the computational device 10.

Step 5: DMA controller 12 configures the three upper (satellite) stations 18 for 4K RSA but does not start them running.

Step 6: DMA controller 12 configures the lowest (base) station 18 for 4K RSA and starts the session running.

Step 7: When session has completed, the base station 18 session controller 24 simultaneously pulses four "done" signals to the DMA controller 12, corresponding to the four session controllers 24 used. This indicates the result is ready for retrieval.

Step 8: The DMA controller 12 transfers the result from the four RSA session RAMs 40.

Step 9: When result has transferred, the DMA controller 12 clears the busy bits for all four of the chosen session controllers 24.

In an embodiment, the bus interface 15 between the computational devices 10 and the DMA controller 12 is composed of a separate thirty-two-bit burst-capable bus interface 16 for each computational device 10. The interface signals all operate from the core clock.

The cleave/merge engine 42 is a controller having a very small datapath and several nested state machines to step through the mathematics of the cleave 30 and merge 34 processes. The datapath consists of a forty-bit wide three-input adder, and several forty-bit accumulators that capture the results. The control logic uses this datapath to perform large multiplies, adds, and subtracts in word-serial fashion. The operands are read from the session RAM 40 one word (thirty-two bits) at a time, and the intermediate and final results are written back to the same memory 40, often overwriting arguments that are no longer needed. In this embodiment, the true size of the operands and results range from 1024 bits for 1K RSA (in a single session RAM 40), to 4096 bits for 4K RSA (split across four RAMs 40).

The Cleave process 30 consists of about ten discrete steps to convert a single 1024-bit operand X (assuming 1K RSA) into two 512-bit results (X mod P and X mod Q). The Merge process takes two 512-bit results from the exponentiators (turrets) 44 and combines them into a single 1024-bit result for the entire RSA exponentiation. The Merge process 34 also involves about ten steps, but one of these is a complete Cleave operation 30 embedded within the Merge 34.

Figure 14:
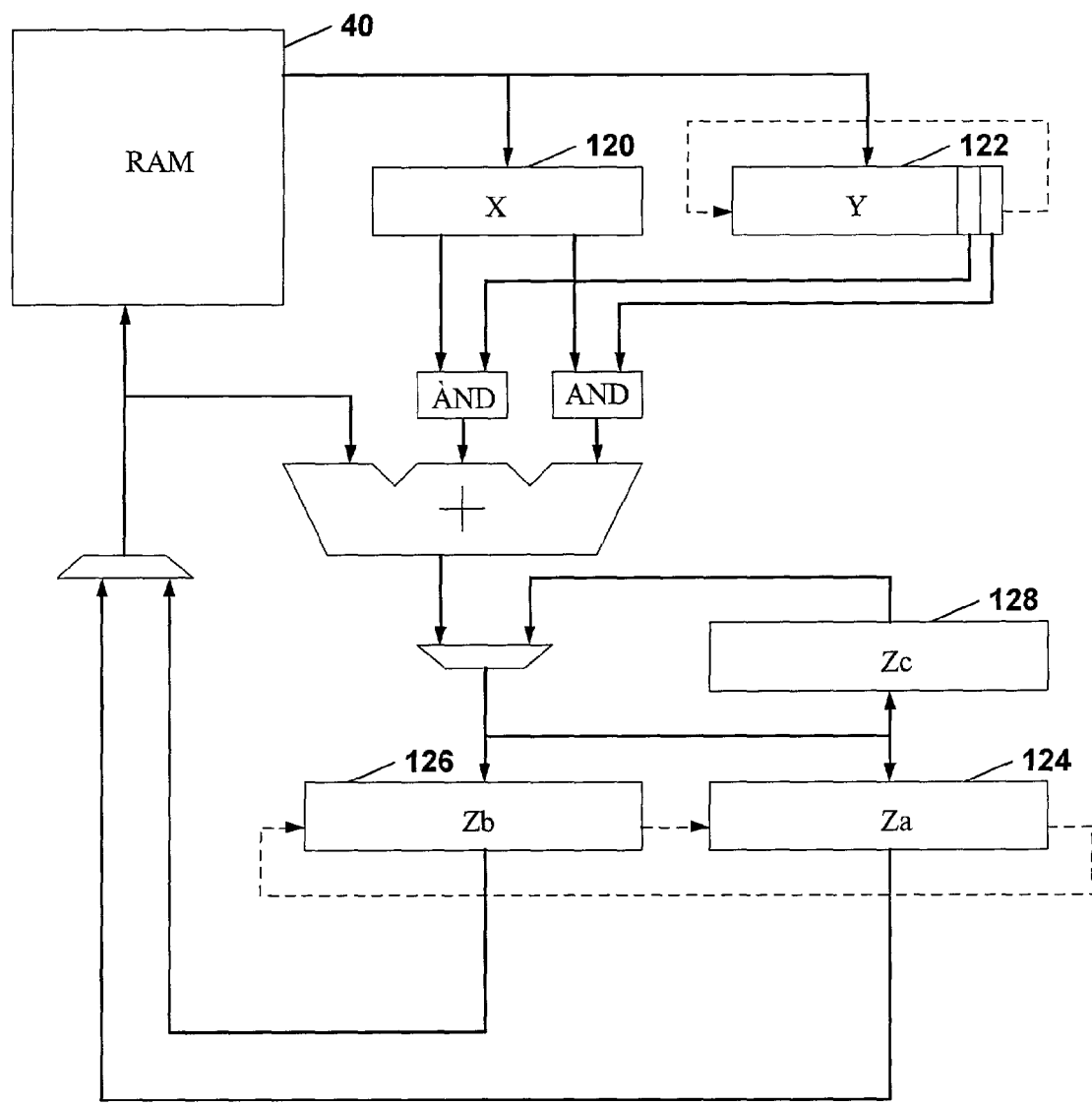
FIG. 14 shows a diagram of a cleave/merge process, in accordance with an embodiment of the present invention.

The steps within cleave 30 and merge 34 that require addition or subtraction complete in about fifty-four clock cycles (for 512-bit operands). The steps that require multiplication complete in about 5000 cycles for a single 512× 512-bit multiply that stores all 1024 result bits. Both of these cycle counts include the time required to read the operands thirty-two bits at a time from RAM 40 and write the results thirty-two bits at a time back to RAM 40. Within the cleave/merge engine 42, the addition, subtraction and multiplication operations are performed by a single datapath that iterates over many cycles while reading operands and writing results in thirty-two-bit increments. FIG. 14 shows a simplified diagram of the cleave/merge datapath.

FIG. 14 illustrates a cleave/merge process for an embodiment. For addition or subtraction, thirty-two-bit slices of the operands X 120 and Y 122 corresponding to the least-significant thirty-two bits are read from RAM 40 into two thirty-two-bit registers. The datapath adds or subtracts the values to produce a thirty-two-bit result, capturing the result in register Za 124. This word is then written back to RAM 40. Next, another thirty-two-bit slice of the operands X 120 and Y 122 are read, corresponding to the next least-significant thirty-two bits, and the process continues until all bits of the operands have been processed, and all bits of the result have been written back to RAM 40. The result could be either 512 bits, 1024 bits, 2048 bits, or 4096 bits, depending on which step of cleave 30 or merge 34 is being processed and whether 1K, 2K, or 4K RSA exponentiation is being performed.

For multiplication, the X 120 and Y 122 operands are also read thirty-two bits at a time, and the results are written back thirty-two bits at a time. The datapath functions as a word-serial multiplier, which performs all processing necessary to produce the final multiplication result as a series of thirty-two-bit result words. It computes and writes the result words to RAM 40 in sequential order, from least-significant word to most-significant word. Because the words of the result are produced in sequential order, the words of the operands are read in a non-sequential, but very specific, order. In fact, most words of the arguments are re-read from RAM 40 many times during the multiplication, since the computation of each result word requires input from many or all of the operand bits. The full size of an operand is 512 bits, 1024 bits, or 2048 bits, and the result is 512 bits, 1024 bits, 2048 bits, or 4096 bits, depending on which step of cleave 30 or merge 34 is being processed and whether 1K, 2K, or 4K RSA exponentiation is being performed.

The multiplication proceeds as follows:

Step 1: Za 124, Zb 126, and Zc 128 registers are initialized to the value zero.

Step 2: A thirty-two-bit slice of the X 120 operand and a thirty-two-bit slice of the Y 122 operand are read from RAM 40 and stored in the X 120 and Y 122 registers.

Step 3: The two least-significant bits of the Y 122 register are multiplied by the thirty-two-bit X 120 register, to produce a thirty-four-bit result.

Step 4: This result is then added (accumulated) into the Zb 126 register.

Step 5: The Zb 126 and Za 124 registers are right-shifted by two bits, and the least significant two bits of Zb 126 are shifted into the two most-significant bits of the Za 124 register.

Step 6: The Y 122 register is also right-shifted by two bits, to place the next least-significant bits at the lowest position in the register, and the two least-significant bits are placed into the two most-significant bits of the Y 122 register (rotated).

Step 7: Steps 3 to 6 are repeated eight times, until all bits of Y 122 have been multiplied by all bits of X 120, and the bits of Y 122 have rotated back around to their original positions. Any overflow bits (carries) from the multiply/accumulate are added to the Zc 128 register.

Step 8: A new thirty-two-bit slice of the operand X 120 (corresponding to the next thirty-two more-significant bits) is read from RAM 40 and placed in the X 120 register.

Step 9: Steps 3 to 8 are repeated until all bits of operand X 120 that are required to produce the current result word have been read. On each repetition, the result is accumulated into either Zb 126 or Za 124 register, alternating on each repetition.

Step 10: A new thirty-two-bit slice of operand Y 122 (corresponding to the next thirty-two more-significant bits) is read from RAM 40 and placed in the Y 122 register Step 11: Steps 3 to 10 are repeated until all bits of operand Y 122 that are required to produce the current result word have been read.

Step 12: The completed thirty-two-bit result word is written back to RAM 40.

Step 13: The carry bits from the previous result word in Zc 128 are copied into the Zb 126 register, and Steps 3 to 13 are repeated until every result word has been computed and written back to RAM 40.

Although this embodiment of the data path uses a word size of thirty-two bits for the widths of registers and RAMs, other embodiments may use a different word size. Also, this embodiment multiplies the X 120 register by two bits of Y 122, and shifts Y 122, Za 124 and Zb 126 by two bits on each clock cycle. Other embodiments may choose to multiply and shift by only one bit on each cycle, or to multiply and shift by three or more bits on each cycle. By using more bits of Y 122 to multiply and shift on each cycle, the overall multiplication will complete in fewer cycles. However, more hardware would be required to multiply the X 120 register by more bits of Y 122 in a single cycle.

The current embodiment uses a shift-and-add multiplier to multiply the X 120 register by two bits of Y 122 in a single cycle. This involves computing X0[31:0]=X[31:0] AND Y[0] (logical AND between least-significant bit of Y 122 and all bits of X 120.) Also computed is X1[31:0]=X[31:0] AND Y[1]. To multiply X 120 by Y[1:0] and accumulate the result into Zb 126, this embodiment uses a three-input adder. The value Zb+2*X1+X0 is computed and captured in Zb 126 (or Za 124). The multiplication of X1 by 2 is a simple left-shift by one bit, and requires no hardware.

When processing a 2K or 4K cleave 30 with merge 34, only a single cleave/merge engine 42 is used. The engine 42 residing in the base station 18 is responsible for reading the words of the larger arguments from the RAMs 40 in the satellite station(s) 18 and writing the results back to those RAMs 40. Because the arguments are still read thirty-two bits at a time, the entire cleave 30 or merge 34 requires four times as many cycles to produce a result for 2K RSA and sixteen times as many cycles to produce a result for 4K RSA. This matches closely with the exponentiator turrets 44, which scale similarly.

Figure 5:
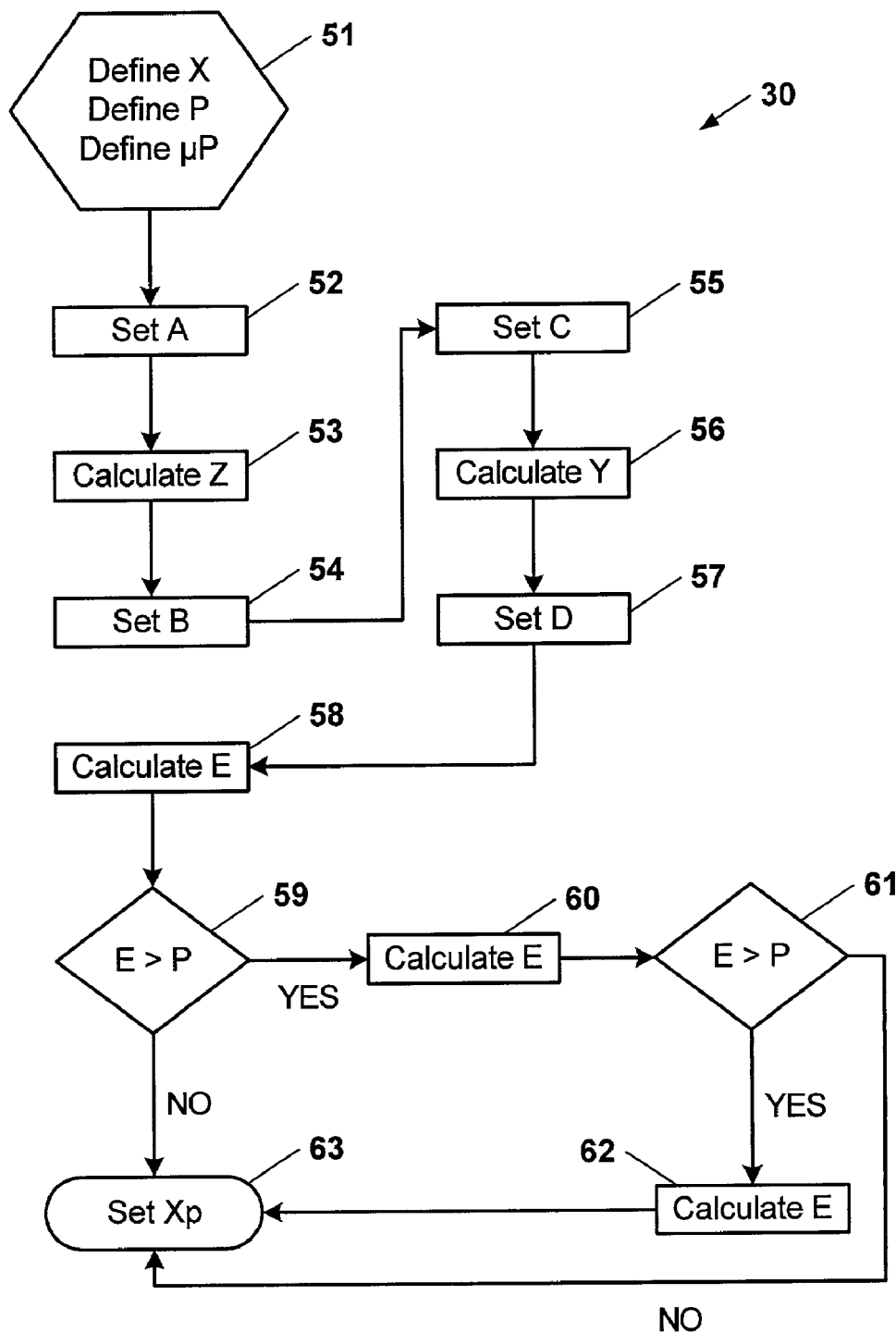
FIG. 5 shows a flowchart of a cleave process, in accordance with an embodiment of the present invention.

FIG. 5 shows a flowchart of a cleave process 30, in accordance with an embodiment of the present invention. The following steps show the mathematics for the Cleave process 30 for 1K RSA. The details of implementation and practical variations are obvious, and this is an accurate high-level representation of an embodiment. All argument sizes double for 2K RSA and quadruple for 4K RSA.

Inputs include X, P, and µP:
X[1023:0] is the data to be cleaved;
P[511:0] is the modulus, could be P or Q; and
µP[512:0] is the mu value, could be µP or µQ. Bit 512 is assumed to be '1'.
The only output is $X_P$:
$X_P$[511:0] is the cleave result, equaling X mod P or X mod Q Cleave procedure steps include:
Step 51: Define inputs X, P, and µP;
Step 52: A[513:0]=X[1023:510];
Step 53: Z[1026:0]=A[513:0]×µP [512:0];
Step 54: B[513:0]=Z[1026:513];
Step 55: C[513:0]=X[513:0];
Step 56: Y[1025:0]=B[513:0]×P[511:0];
Step 57: D[513:0] Y[513:0];
Step 58: E[513:0]=C[513:0]−D[513:0];
Step 59: if E>P then E=E−P in 60;
Step 61: if E>P then E=E−P in 62; and
Step 63: return $X_P$=E[511:0].

Note that A and B can be implemented in different lengths than shown in this embodiment.

Figure 6:
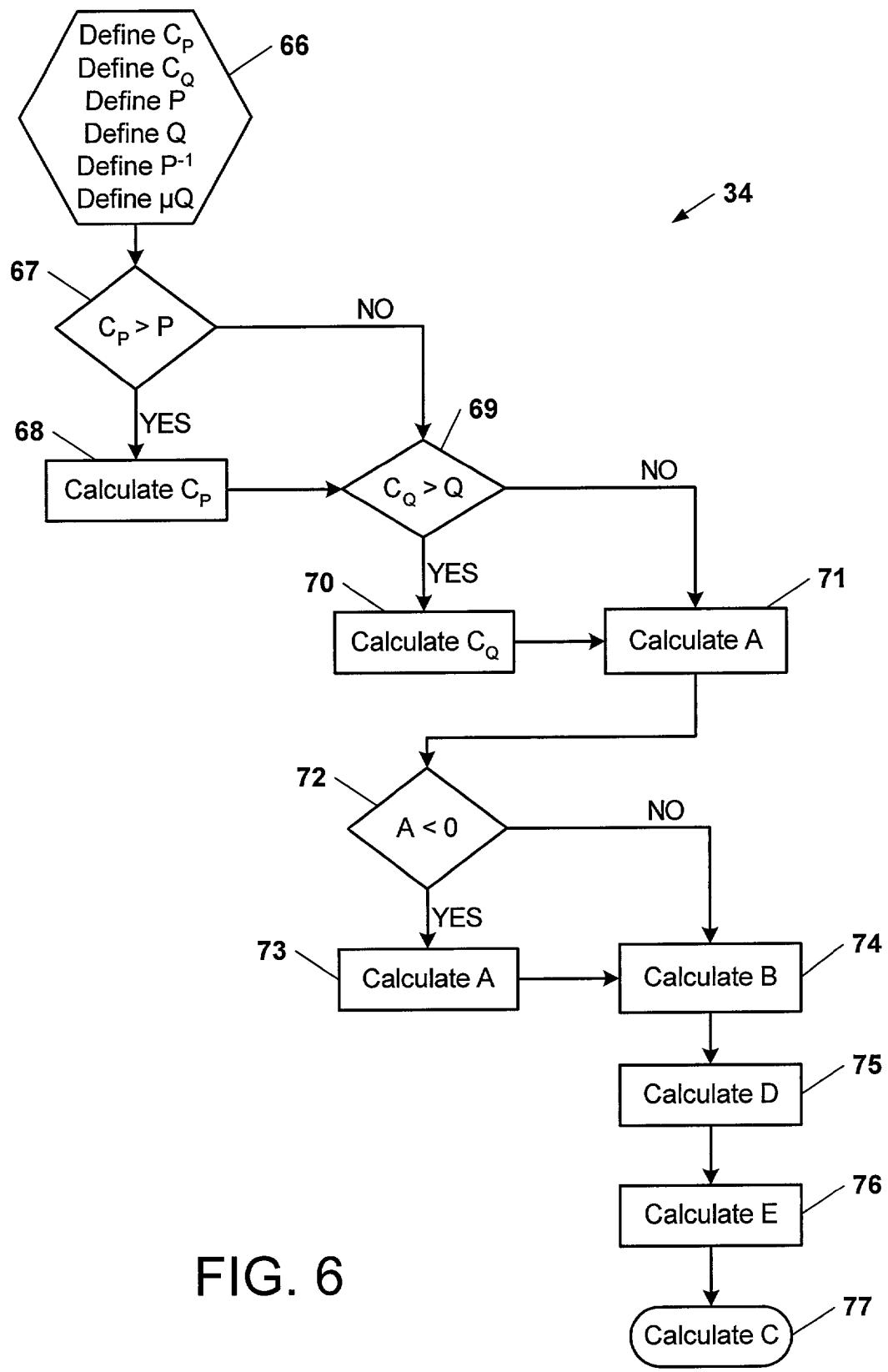
FIG. 6 shows a flowchart of a merge process, in accordance with an embodiment of the present invention.

FIG. 6 shows a flowchart of a merge process 34, in accordance with an embodiment of the present invention. The following steps show the mathematics for the Merge process 34 for 1K RSA. The details of implementation and practical variations are obvious, and this is an accurate high-level representation of an embodiment. All argument sizes double for 2K RSA and quadruple for 4K RSA.

Inputs include $C_P$, $C_Q$, P, Q, $P^{-1}$, and µQ:
$C_P$[511:0] is the data to be merged;
$C_Q$[511:0] is the data to be merged;
P[511:0] is the modulus;
Q[511:0] is the modulus;
$P^{-1}$[511:0] is the inverse of P mod Q; and
µQ[512:0] is the mu value, needed for embedded cleave. Bit 512 is assumed to be '1'.
The only output is C:
C[1023:0] is the decrypted data.

Merge procedure steps include:
Step 66: Define $C_P$, $C_Q$, P, Q, $P^{-1}$, and µQ;
Step 67: if $C_P$>P then $C_P=C_P$−P, in 68;
Step 69: if $C_Q$>Q then $C_Q=C_Q$−Q 70;
Step 71: A[512:0]=$C_Q$[511:0]−$C_P$[511:0];
Step 72: if A<0 then A[511:0]=A[511:0]+Q[511:0] in 73;
Step 74: B[1023:0]=A[511:0]×$P^{-1}$[511:0];
Step 75: D[511:0]=Cleave B[1023:0] mod Q[511:0];

wherein Cleave is the process described above with input B for X, input Q for P, input µQ for µP, and output D for $X_P$.

Step 76: E[1023:0]=D[511:0]×P[511:0]; and
Step 77: return C[1023:0]=E[1023:0]+$C_P$[511:0].

In an alternative embodiment, Diffie-Hellman exponentiation can be performed instead of RSA exponentiation. The session controller 24 would be configured accordingly. There are several important differences between RSA exponentiation and Diffie-Hellman:
(1) There is a different set of input arguments;
(2) The user must enable and use the session controller 24 to control the turrets 44;
(3) The cleave process 30 must be disabled in the session controller 24;
(4) Only "P" turrets 44 are used. "Q" turrets 44 sit idle during exponentiation 32; and
(5) The merge process 34 is enabled, but is a greatly simplified procedure that only performs a single conditional subtraction (steps 67 and 68).

The cleave process 30 and Q turrets 44 cannot be used because the modulus for Diffie-Hellman is a prime number, rather than the product of two primes as in RSA. This means that such an embodiment only supports Diffie-Hellman exponentiation of half the size of a similar RSA exponentiation. Thus, this embodiment supports Diffie-Hellman key sizes of 512 bits, 1K, and 2K.

In an embodiment, a turret 44 handles the processing for an exponentiation session and includes the state machines necessary to take the basic input from the Cleave/Merge Engine 42 and provide it with a single result in return. The 512-bit turrets 44 can be chained to act as a larger exponentiator. In this embodiment, a turret 44 can handle either RSA or Diffie-Hellman exponentiation 32. There are state control differences between them, but the base computation is done with the same underlying hardware.

In an embodiment, the RSA exponentiation process 32 proceeds thus:
Step 1: X[511:0] is a pointer to memory device 38;
Step 2: $D_{127}D_{126}D_{125} \ldots D_1D_0$ are the four-bit nibbles of $D_P$ (or $D_Q$);
Step 3: $R_0 \ldots R_{15}$ are powers registers;
Step 4: $R_0$=1;
Step 5: $R_1$=X;
Step 6: For i=2 to 15: $R_i$=BMULT$_P R_{i-1}$, $R_1$;
Step 7: t=$D_{127}$;
Step 8: X=$R_t$;
Step 9: For j=126 to 0 (step −1): For i=1 to 4: X=BMULT$_P$X, X <end i loop>t=$D_j$ and X=BMULT$_P$X, $R_t$; and
Step 10: return $X^{Dp}$ mod P (or $X^{DQ}$ mod Q) as X=BMULT$_P$ X, $2^{\delta(P)}$ (or BMULT$_Q$X, $2^{\delta(Q)}$)

In this embodiment, Broadside Multiply (BMULT$_P$ A, B) is defined thus:
Step 1: A, B, and modulus P are 512-bit numbers;
Step 2: S, D, C, $C_1$, $C_2$, $X_1$, and $X_2$ are 515-bit registers;
Step 3: S=0, C=0, D=0;
Step 4: For i=0 to 255:
Step 4.1: $\lambda_1$=$S_0$ XOR $C_0$ XOR $D_0$; $\lambda_2$=$S_1$ XOR $C_1$ XOR $D_1$ XOR $\lambda_1 P_1$ XOR $((S_0 \vee C_0 \vee D_0)$~$(S_0\hat{}C_0\hat{}D_0))$;
Step 4.2: $C_1$=$\lambda_1$P; $C_2$=2$\lambda_2$P;
Step 4.3: $X_1$=4A[2i]B; X2=8A[2i+1]B;
Step 4.4: S, C, D=7:3 compress S, C, D, $C_1$, $C_2$, $X_1$, $X_2$;
wherein "7:3 compress" means taking a set of seven one-bit-wide values and producing the binary representation for the number of ones in that set;
Step 4.5: S=S/4, C=C/4, D=D/4;
Step 5: R=S+C+D (full add);
Step 6: If $R_{512}$=1 (R>$2^{512}$) then R=R−P;
Step 7: return R=AB$2^{-512}$ mod P (can return x+P for x)

A Diffie-Hellman exponentiation process proceeds similarly to the RSA exponentiation process disclosed above, with a few simple changes that are obvious to those of ordinary skill in the art.

Figure 7:
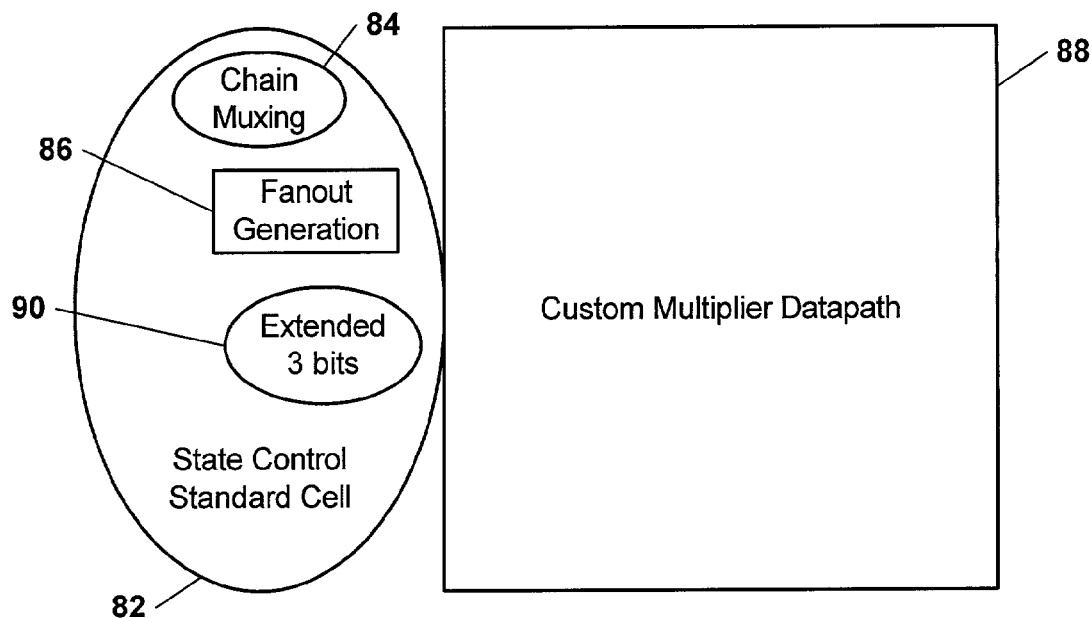
FIG. 7 shows a conceptual diagram of an exponentiator, in accordance with an embodiment of the present invention.

FIG. 7 shows a conceptual diagram of an exponentiator, in accordance with an embodiment of the present invention. In an embodiment, the core of the exponentiation hardware is a custom Montgomery multiplier controlled by a state machine 82. In this embodiment, the 512-bit implementation is described as the base. The custom hardware is capable of retiring eight bits per computational device clock cycle when doing a multiply. This effectively compresses the inner loop of the BMULT process described in this application by a factor of four in clock cycles. Intermediate values from cycle to cycle are kept in redundant form to remove carry propagation. FIG. 7 shows the turret 44 logical block diagram.

The chain muxing 84 block provides muxes to connect multiple 512-bit turrets 44 together to form larger multipliers (1024- and 2048-bit, in this embodiment). Fanout generation 86 produces the eight fanout values used by the multiplier datapath 88. It contains a nearly redundant copy of the first eight bits of the custom multiplier datapath 88 to allow each turret 44 produce the same fanout values when being chained. The extended three bits 90 contains an extended three bits of the multiplier array that is necessary to perform the process. The state control standard cell 82 has the hardware state machines that control the exponentiation process 32 and handle all of the register map functions of the block. The custom multiplier datapath 88 is a highly tuned array optimized for both speed and power. It is described in more detail in this application.

In this embodiment, fanout generation block is a custom hard macro, and the chain muxing and extended three bits blocks are standard-cell-based physical implementations.

Figure 8:
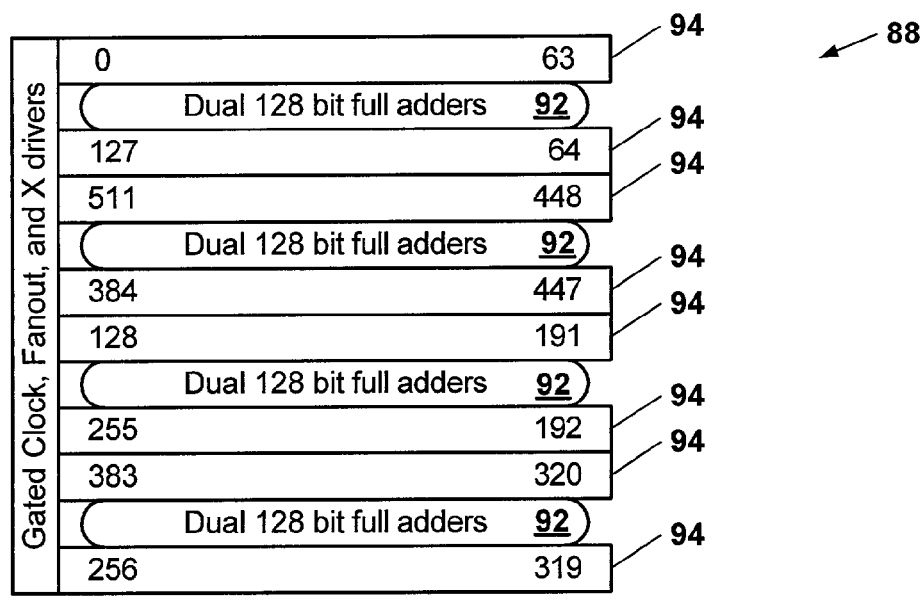
FIG. 8 shows a custom multiplier datapath, in accordance with an embodiment of the present invention.

FIG. 8 shows the organization of the custom multiplier datapath 88, in accordance with an embodiment of the present invention. Repetitive bit slices 96 form the datapath 88, organized in this embodiment as eight rows of sixty-four bits. The connectivity is in a serpentine fashion to minimize routing length differences at the end of rows and when chaining 512-bit turrets 44 together to form larger exponentiators 44. The one-hundred-twenty-eight-bit adder 92 between paired rows 94 is used between successive multiplies to form the finished product. For computing an exponentiation 32, a sixteen-entry register file is used to hold the first sixteen powers of the initial X value in RSA exponentiation 32. This reduces the overall multiplies necessary to complete the exponentiation 32 and creates a limited worst-case number of cycles.

Figure 9:
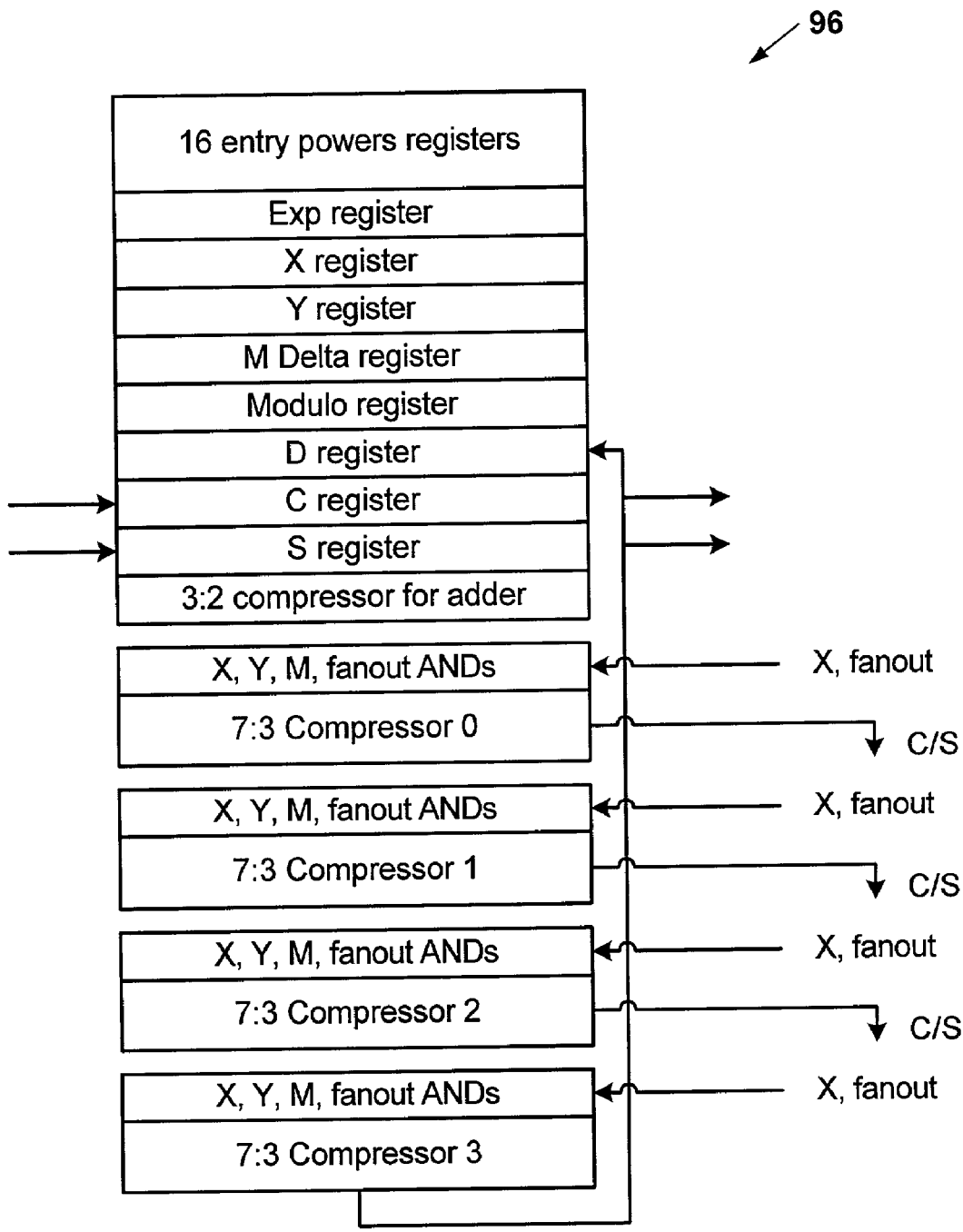
FIG. 9 shows a custom multiplier bit slice, in accordance with an embodiment of the present invention.

As with all figures, FIG. 8 is not representative of scale. In this embodiment's physical implementation, the individual rows are much taller than the dual adders. The adders are standard cell place and route components rather than custom because of the connectivity. They are included within the custom row organization to avoid routing approximately 1500 wires in and out of the block. FIG. 9 shows the logic contained within a bit slice 96 of the multiplier 88. This logic has been custom tuned for power and performance.

As shown in FIG. 3, an embodiment groups four turrets 44 together physically. They are grouped in four so that the individual turrets 44 can be chained to form four 512-bit, two 1024-bit, one 1024-bit with two 512-bit, or one 2048-bit exponentiator. Within a computational device 10, two blocks of turrets 44 are placed to form the "P" and "Q" exponentiate functions.

One of the issues with the style of multiplier implemented in an embodiment of this design is that the high fanout control signals—i.e., the lower eight bits of the multiplicand and the modulo add select control for the Montgomery multiplier process—must be distributed to each bit slice 96 used in the multiplication. As an example, for the 2048-bit multiply, all 2048 bits must see the control signals. To both avoid mux 84 delays in these critical paths and provide speed-optimized logic for generating those signals, the lower eight bits of the multiplier are duplicated in the fanout generation block 86 for each turret 44. When chaining two or four turrets 44 together all of the local high fanout generation blocks 86 and state machine controllers 82 are loaded with the same values. This keeps them in lock step through the computation and eliminates the need for significant muxing 84 of control signals. There are still some data signals that require muxing 84, such as full adder carries, but using the individual control blocks in a redundant form significantly reduces the complexity. As a result of these optimizations there is no clock rate penalty for using 2K or 4K RSA due to high fanout. Such exponentiations only take time based on the size of the operands.

Figure 10:
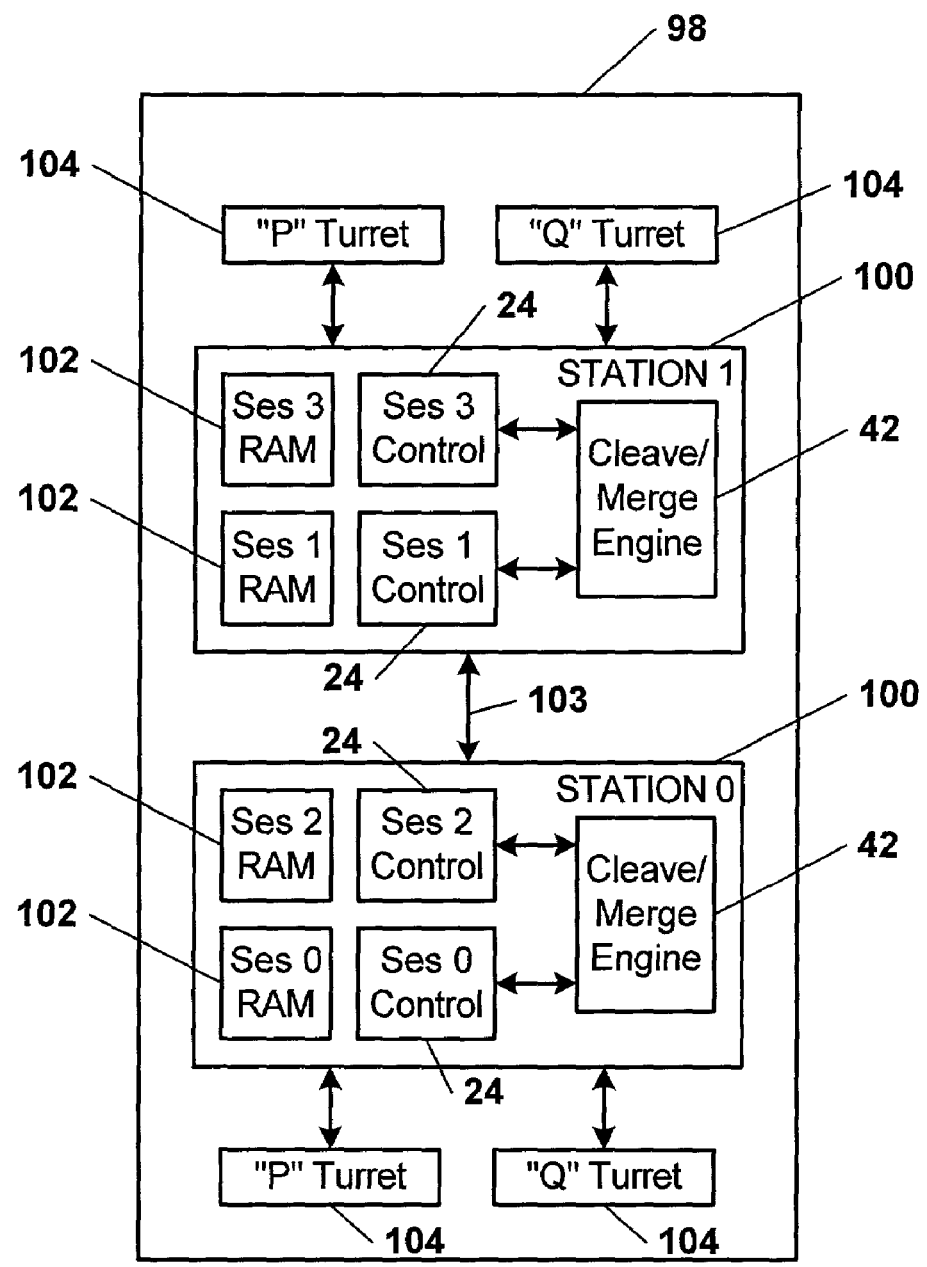
FIG. 10 shows a conceptual organization of a computational device having two stations, in accordance with an embodiment of the present invention.

FIG. 10 shows a conceptual organization of a computational device 98 having two 1024-bit stations 100, in accordance with an embodiment of the present invention. Thus, the two stations 100 can be chained together 103 to perform 2048-bit exponentiation 32. Each station 100 has a cleave/merge engine 42. Two session controllers 24 share each cleave/merge engine 42, and each session controller 24 has its own session RAM 102. "P" and "Q" turrets 104 are available to each station 100 to perform exponentiation 32.

Figure 11:
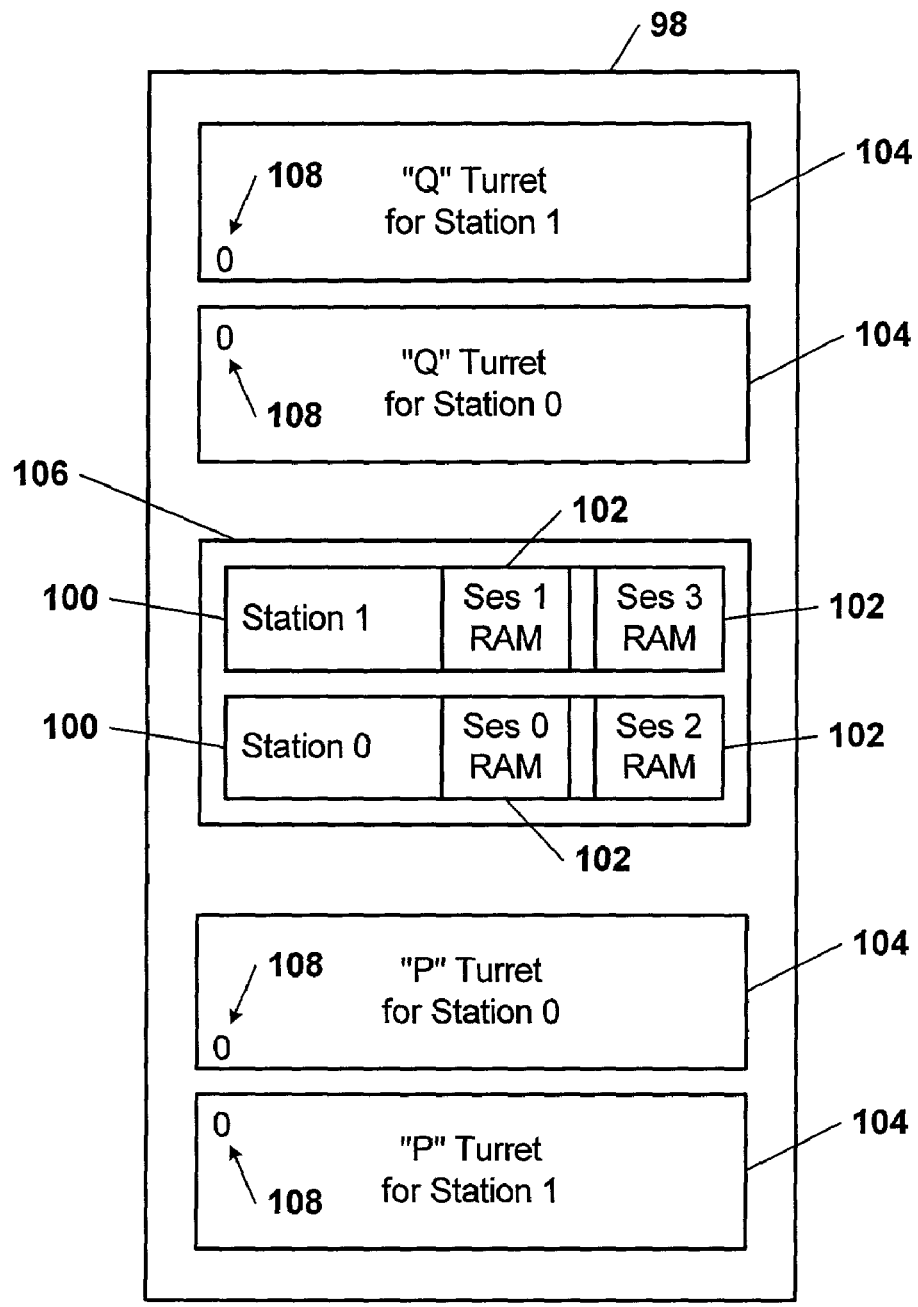
FIG. 11 shows a physical organization of a computational device having two stations, in accordance with an embodiment of the present invention.

FIG. 11 shows a physical organization of the computational device 98 having two stations 100, in accordance with this embodiment of the present invention. A control block 106 includes the two stations 100, with their session RAMs 102. The turrets 104 are mirrored in both X and Y dimensions to place the least significant register bits 108 from each turret 104 near each other for improved chaining 103 performance.

Figure 12:
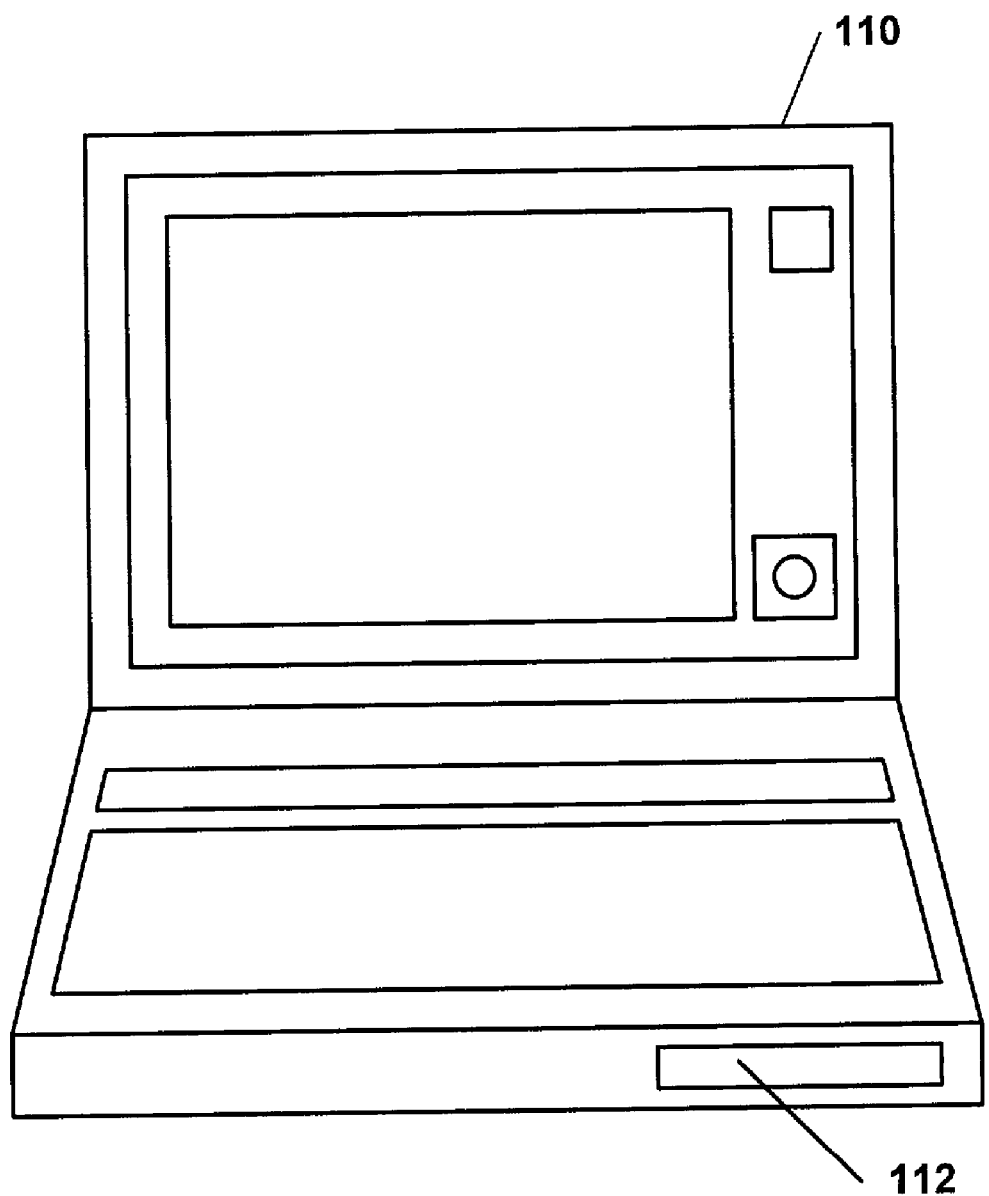
FIG. 12 shows a notebook computer with a computational plug-in, in accordance with an embodiment of the present invention.

FIG. 12 shows a notebook computer 110 with an accelerated computational plug-in 112, in accordance with an embodiment of the present invention. In this embodiment, the computer 110 utilizes the computational plug-in 112 to perform accelerated computations. In an embodiment, the computational plug-in 112 performs accelerated exponentiation.

Figure 13:
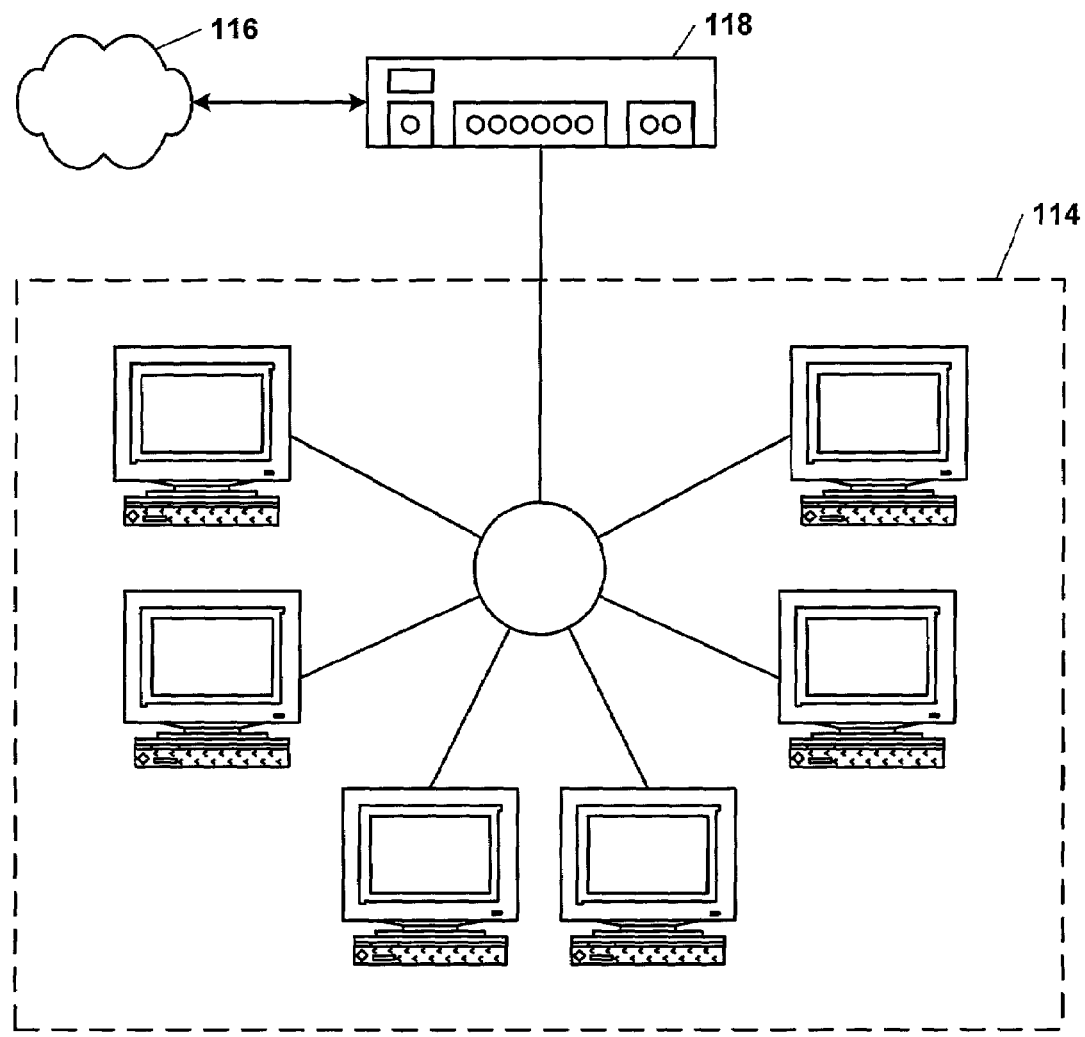
FIG. 13 shows a network connected to the Internet via a computationally enabled hub, in accordance with an embodiment of the present invention.

FIG. 13 shows a network 114 connected to the Internet 116 via a computationally enabled hub 118, in accordance with an embodiment of the present invention. In this embodiment, one function of the hub 118 is to decrypt encrypted packets as they arrive from the Internet 116 destined for the network 114. Another function of the hub 118 is to encrypt packets as they are sent from the network 114 out over the Internet 116. The hub 118 is able to encrypt and decrypt packets quickly because it embodies a Computational Method, System, and Apparatus of the present invention. In this embodiment, the computation is exponentiation. The accelerated exponentiation achieves a capacity for accelerated decryption and accelerated encryption.

Note that while the cleave process 30 and the merge process 34 are described throughout most of this application as being in a single cleave/merge engine, they are separate engines in other embodiments. Likewise, many such variations are obvious with respect to various aspects of the embodiments discussed that do not depart from the scope of the present invention.

Any logic described in this application can be synthesized or custom routed without departing from the scope of the present invention.

APPENDIX A—GLOSSARY

This Glossary defines words as they are used throughout this application. This Glossary lists base words rather than word variations. But the meanings of word variations—such as "connecting," "connect," and "connected" for the base word "connection"—are also given meaning according to their logical relationship to the base word.

"=" means equality or congruence, depending on the context. This is clear to typical practitioners of this technical area.

"~" means approximately.

"1K" means 1024.

"2K" means 2048.

"4K" means 4096.

"Φ[α]" means Φ's α-th bit.

"Φ[α:β]" means a binary number composed of the bit sequence of Φ that starts with Φ's α-th bit and ends with Φ's β-th bit. For example, if Φ is a 512-bit number, it would typically be represented in its entirety as Φ[511:0]; its highest ten bits would be represented by Φ[511:502].

"Algorithm" means a process for completing a task. An encryption algorithm is the process, typically with mathematical characteristics, to encrypt and decrypt messages.

"ARP" means Address Resolution Protocol. To map an IP address into a hardware address, a computing device uses the ARP protocol which broadcasts a request message containing an IP address, to which a target computing device replies with both the original IP address and the hardware address.

"Asymmetric encryption" means encryption used in a public-private key cryptosystem.

"Asymmetric key cipher" means a public-private key cryptography system.

"Authentication" means the process of verifying that a file or message has not been altered in route from the distributor to the recipient(s).

"Chaining controller" means a controller that associates stations as a computational chain. One example of a chaining controller is the Security Protocol Processor DMA Engine that chains exponentiators into an exponentiation chain.

"Cipher" means a cryptographic algorithm used to encrypt an decrypt files and messages.

"Ciphertext" means the disguised (or encrypted) file or message.

"Computational chain" means two or more stations that are chained together to perform a computation beyond the capacity of a single station.

"Computational device" means a device that is given an input, computes a result based on the input, and outputs the result. A computational device is an example of a computational device.

"Computing device" means a device having at least one processor and at least one memory device, wherein the processor can process data that can be stored in the memory device before and/or after processing, or a group of devices having that capacity in combination. By this definition, examples of a computing device include computer personal computer, palm computing device, notebook computer, server, mainframe, network of computing devices with coordinated processing or storage, network of components functioning together as a computing device wherein any single component may not be a computing device in its own right, etc. As another example, components of a computing device may be connected across the Internet. Other examples of computing devices could include boards, chips, exponentiators, multipliers, etc.

"Connection" means any connection that is adapted to carry communication, whatever the supporting technology. Examples of connections include hard wire connections such as phone lines, T1 lines, DSL, fiber optic, Ethernet, twisted pair, etc. Other examples of connections include wireless connections such as those operating by electromagnetic waves, wireless optics (e.g., infrared), etc. Further examples are a logical connection between two processes on the same system, and a connection between two processes sharing a common memory space.

"Coprime" is defined such that if P and Q are coprime, their greatest common divisor is 1.

"Cryptanalysis" means the art of breaking cryptosystems. It also means the process of looking for errors or weaknesses in the implementation of an algorithm or of the algorithm itself.

"Cryptography" is the art of creating and using cryptosystems.

"Cryptosystem" means the entire process of using cryptography. This includes the actions of encrypting and decrypting a file or message. It also means authenticating the sender of an e-mail message.

"Decryption" means any process to convert ciphertext back into plaintext. Decrypting is synonymous to decoding.

"DDR-SDRAM" means SDRAM that supports data transfers on both edges of each clock cycle (the rising and falling edges). DDR-SDRAM is an abbreviation of Double Data Rate Synchronous DRAM and is also called SDRAM II.

"DES" means the Data Encryption Standard. It is a cipher developed by the United States government in the 1970s to be the official encryption algorithm of the United States.

"Digital signature" means systems that allow people and organizations to electronically certify such features as their identity, their ability to pay, or the authenticity of an electronic document.

"DRAM" means RAM that must be continually refreshed or it will lose its state (on/off), making it slower than SRAM at this time. DRAM is an abbreviation for Dynamic RAM and is the most widely used RAM in PCs at this time.

"Encryption" means any process to convert plaintext into ciphertext. Encrypting is synonymous to encoding.

"Exponentiation chain" means two or more stations that are chained together to perform a exponentiation beyond the capacity of a single station.

"Exponentiator" means a computational device that performs exponentiation.

"Fanout" means distributing a signal to multiple destinations.

"FTP" means File Transfer Protocol. FTP enables transferring of text and binary files over TCP connections. FTP allows transferring files according to a strict mechanism of ownership and access restrictions. It is now one of the most commonly used protocols over the Internet.

"Hamming weight" means the number of "1" bits in the binary representation of a number.

"High fanout" means distributing a signal to a great enough number of destinations that a significant delay occurs before all the destinations receive the signal.

"HTTP" means Hyper Text Transfer Protocol. It is a protocol used to transfer hypertext pages across the World Wide Web.

"IP" means Internet Protocol, and is the underlying protocol for the other Internet protocols. IP defines the means to identify and reach a target computer on the network. A unique number known as an IP address identifies each computing device in the IP world.

"IPSec" means Internet Protocol Security. It is a standard for security at the network or packet-processing layer of network communication. IPSec provides two choices of security service: Authentication Header (AH), which essentially allows authentication of the sender of data, and Encapsulating Security Payload (ESP), which supports both authentication of the sender and encryption of data. IPSec is a suite of protocols that protect client protocols of IP, such as TCP. IPSec describes mechanisms that provide data source authentication, data integrity, confidentiality and protection against replay attacks. IPSec provides transport mode and tunnel mode operation. Some embodiments provide only tunnel mode operation, and others offers a more complete IPSec implementation.

"iSCSI" is a software package that emulates SCSI protocols, but the connection method is via an IP network instead of a direct SCSI compatible cable. This is one example of IP-based storage.

"Key" means a collection of bits, usually stored in a file, which is used to encrypt or decrypt a message.

"Network protocol" means a standard designed to specify how computers interact and exchange messages. It usually specifies the format of the messages and how to handle errors. The following Internet protocols are examples of network protocols: ARP, FTP, HTTP, IP, NNTP PPP, SLIP, SMTP, SNMP, TCP, Telnet, and UDP.

"NNTP" means Network News Transfer Protocol. It is a protocol used to carry USENET postings between News clients and USENET servers.

"PGP" means Pretty Good Privacy. It is a public-private key cryptosystem that allows users to more easily integrate the use of encryption in their daily tasks, such as e-mail protection and authentication, and protecting files stored on a computer. PGP is available for free to individual home users.

"Plaintext" means the original message or file. After a file or message has been encrypted and then decrypted you should end up with the original file or message.

"PPP" means Point-To-Point protocol, and is a protocol for creating a TCP/IP connection over both synchronous and asynchronous systems. PPP provides connections for host-to-network or router-to-router. It also has a security mechanism. PPP is well known as a protocol for connections over regular telephone lines using modems on both ends. This protocol is widely used for connecting personal computers to the Internet.

"Private key" means the private key of a public-private key cryptosystem. This key is used to digitally sign outgoing messages and is used to decrypt incoming messages.

"Public key" means the public key of a public-private key cryptosystem. This key is used to confirm digital signatures on incoming messages or to encrypt a file or message so that only the holder of the private key can decrypt the file or message.

"Public key cryptosystem" means an asymmetric encryption algorithm in which it is infeasible to derive one key from the other.

"Public-private key cryptosystem" means a cryptosystem that uses two different keys to encrypt and decrypt messages and files. The two keys are mathematically related to each other, but deriving one key from the other is infeasible. One key is a public key and one key is a private key. The public key is usually distributed to other users, and the private key is usually kept secret.

"RAM" means computer memory that can be accessed randomly. Data can be read from or written to any portion of RAM, regardless of its position. RAM is an abbreviation for Random Access Memory.

"Replicating fanout logic" means distributing mirrored state information so that multiple controllers can operate based on the same state information without delay based on a high fanout.

"Ring arithmetic" means an arithmetic of mathematical structures in which addition, subtraction, multiplication, and their obvious consequences such as exponentiation, have the properties and interrelationships usually encountered in high school algebra.

"RSA exponentiation" means the process for both encryption and decryption in the RSA public-key process. It entails the computation of $A^b$ mod m, where b and m are elements of the key and A is the data to be encrypted or decrypted.

"RSA session" means a session launched by an exponentiator to compute an exponentiation.

"SCSI" is an intelligent protocol that enables data blocks to be read at high speed from or sent at high speed to storage devices such as disks or tape drives. Early implementations of SCSI used ribbon cable and industry standard logic levels.

"SDRAM" means DRAM that has its operations synchronized to an external clock. SDRAM is an abbreviation for Synchronous DRAM.

"Security association" means a relationship between two or more entities that describes how the entities will utilize security services to communicate securely. This relationship is represented by a set of information that can be considered a contract between the entities. The information must be agreed upon and shared between all the entities. Security association is commonly abbreviated SA.

"Shotgun multiplication" means a process like that described in this application for performing fast computations by performing processing in mathematically independent units, taking advantage of more than one basis and precomputed operands, and accommodating iterative problems.

"SLIP" means Serial Line Internet Protocol, and is a point-to-point protocol to use over a serial connection, a predecessor of PPP. There is also an advanced version of this protocol known as CSLIP (compressed serial line internet protocol) that reduces overhead on a SLIP connection by sending just header information when possible, thus increasing packet throughput.

"SMTP" means Simple Mail Transfer Protocol, and is dedicated to sending e-mail messages originating on a local host to a remote server over a TCP connection. SMTP defines a set of rules that allows two programs to send and receive e-mail over the network. The protocol defines the data structure to deliver with information regarding the sender, the recipient(s) and the e-mail's body.

"Snapshotting" means recording the present state of potentially changing values so that the values can be treated as fixed.

"SNMP" means Simple Network Management Protocol. It is a simple protocol that defines messages related to network management. Through the use of SNMP, network devices such as routers can be configured by any host on their network.

"SRAM" means RAM that is generally faster at accessing random data than DRAM. But at this time SRAM is more expensive and requires more power. SRAM is an abbreviation for Static RAM.

"SSL" means Secure Sockets Layer, and is a trademark of Netscape. It is a program layer created by Netscape for managing the security of message transmissions in a network. The concept is that the programming for keeping messages confidential is to be contained in a program layer between an application (such as a Web browser or HTTP) and the Internet's TCP/IP layers. The "sockets" part of the term refers to the sockets method of passing data back and forth between a client and a server program in a network or between program layers in the same computer.

"SSL/TLS" means compatible with SSL and with TLS.

"Symmetric key" means the key of a symmetric key cryptosystem. The symmetric key is used to encrypt a file or message and also to decrypt the file or message.

"Symmetric key cryptosystem" means a cryptosystem that uses one key to lock and unlock—encrypt and decrypt—messages and files. The sender must posses the key to encrypt a file or message, and the recipient(s) must possess the key to decrypt the file or message.

"TCP" means Transmission Control Protocol. Like UDP, TCP is a protocol that enables a computer to send data to a remote computer. But unlike UDP, TCP is reliable—packets are guaranteed to wind up at their target in the correct order.

"Telnet" is a terminal emulation protocol for use over TCP connections. It enables users to login to remote hosts and use their resources from the local host.

"TLS" means Transport Layer Security. It is the successor protocol to SSL, created by the Internet Engineering Task Force (IETF) for general communication authentication and encryption over TCP/IP networks. TLS version 1 is nearly identical with SSL version 3, providing data integrity and privacy on a communications link over the Internet. It allows client-server applications to communicate and is designed to prevent eavesdropping, message forgery, and interference.

"TOE" means TCP Offload Engine. TOE technology typically takes the server CPU out of I/O processing by shifting TCP/IP processing tasks to a network adapter or storage device. This leaves the CPU free to run its applications, so users get data faster.

"Triple DES" means a method of improving the strength of the DES algorithm by using it three times in sequence with different keys.

"UDP" means User Datagram Protocol. It is a simple protocol that transfers datagrams (packets of data) to a remote computer. UDP doesn't guarantee that packets will be received in the order sent or that they will arrive at all.

"Wire speed" means the rate of data transfer a given telecommunication technology provides at the physical wire level. Wire speed also means any equipment or function that tends to support this data transfer rate without slowing it down. It is common to refer to functions embedded in microchips rather than in software programming as working at wire speed. Some switches, routers, and other devices operate at, or close to, wire speed. Some encryption, decryption, hardware emulation, other software functions operate at, or close to, wire speed when embedded in a microchip.

Any element in a claim that does not explicitly state "means for" performing a specified function, or "step for" performing a specific function, is not to be interpreted as a "means" or "step" clause as specified in 35 U.S.C. § 112, ¶ 6. In particular, the use of "step of" in the claims herein is not intended to invoke the provision of 35 U.S.C. § 112, ¶ 6.

It should be apparent from the foregoing that an invention having significant advantages has been provided. While the invention is shown in only a few of its forms, it is not just limited to those forms but is susceptible to various changes and modifications without departing from the spirit thereof.

What is claimed is:

1. An apparatus for performing exponentiations, comprising:
    a set of computational devices containing first and second subsets, wherein the first subset has a plurality of members which are chained together such that the devices of the first subset can operate both independently and as members of a first computational chain, and wherein the second subset has a plurality of members which are chained together such that the devices of the second subset can operate both independently and as members of a second computational chain distinct from said first computational chain; and
    a chaining controller adapted to instruct the first subset of devices to act as a first computational chain when the apparatus is required to perform an exponentiation of a first size, and being further adapted to instruct the second subset of devices to act as a second computational chain when the apparatus is required to perform an exponentiation of a second size distinct from said first size;
    wherein each computational device is adapted to perform 1024-bit exponentiation, wherein said chaining controller is adapted to instruct the first subset of devices to act as a first computational chain when the apparatus is required to perform 2048-bit exponentiation, and wherein said chaining controller is adapted to instruct the second subset of devices to act as a second computational chain when the apparatus is required to perform 4096-bit exponentiation.

2. The apparatus of claim 1, further comprising a hardware state controller for each computational device of the first computational chain, wherein each hardware state controller includes replicated fanout control logic.

3. The apparatus of claim 2, wherein the replicated fanout control logic is configured to allow computational devices of the first computational chain to chain without delay due to high fanout.

4. The apparatus of claim 2, wherein the replicated fanout control logic is configured such that state machines of the first computational chain sequence efficiently.

5. The apparatus of claim 1, wherein each computational device further comprises a custom multiplier datapath, and wherein each custom multiplier datapath is configured so that the length of its longest wire is short.

6. The apparatus of claim 5, wherein the custom multiplier datapaths of chained computational devices are physically mirrored to each other so that the wire length between the two is short.

7. The apparatus of claim 5, wherein the custom multiplier datapath has a serpentine layout so that the wire length between the most separated adjacent data locations is short.

8. The apparatus of claim 1, wherein the number of computational devices in the set of computational devices equals $2^k$, and wherein k is a non-negative integer.

9. The apparatus of claim 8, wherein k equals 2.

10. The apparatus of claim 8, wherein each computational device is adapted to exponentiate a 512-bit number.

11. The apparatus of claim 1, wherein the number of computational devices in the first computational chain equals $2^k$ wherein k is a positive integer.

12. The apparatus of claim 11, further comprising:
    a second computational chain;
    wherein the second subset includes at least two computational devices, wherein the chaining controller is configured to instruct the second subset to operate as a second computational chain, and wherein no computational device of the first computational chain is part of the second computational chain.

13. The apparatus of claim 1, wherein each computational device in said set of computational devices further comprises:
    a cleave/merge engine;
    wherein the cleave/merge engine is configured to:
        receive AA, which is a 2 w-bit number;
        calculate $A_1$ and $A_2$, which are two w-bit numbers based on AA; and
        output $A_1$ and $A_2$;
    wherein the cleave/merge engine is also configured to:
        receive $B_1$ and $B_2$, which are two w-bit numbers;
        calculate BB, which is a 2 w-bit number based on $B_1$ and $B_2$; and output BB;
    wherein exponentiation of AA yields BB;

wherein exponentiation of $A_1$ yields $B_1$;
wherein exponentiation of $A_2$ yields $B_2$; and
wherein w is a positive integer.

14. The apparatus of claim 13, wherein $A_1$ and $A_2$ are calculated from AA, and BB is calculated from $B_1$ and $B_2$, using a scalable Chinese Remainder Theorem implementation.

15. The apparatus of claim 14,
wherein each computational device is adapted to perform 1024-bit exponentiation;
wherein, if 2048-bit exponentiation is required, the chaining controller causes the first computational chain to comprise two exponentiators; and
wherein, if 4096-bit exponentiation is required, the chaining controller causes the first computational chain to comprise four exponentiators.

16. The apparatus of claim 1, wherein said chaining controller is adapted to implement a flexible chaining algorithm.

17. The apparatus of claim 1, wherein the first computational chain comprises two computational devices, and wherein the second computational chain comprises four computational devices.

18. The apparatus of claim 1, wherein at least some of the computational devices in the first computational chain are also in the second computational chain.

19. A method for encrypting/decrypting data comprising:
providing a 1024-bit number X; and
encrypting/decrypting X by
loading X into session memory,
cleaving X mod P to compute $X_P$,
cleaving X mod Q to compute $X_Q$,
exponentiating Xp to compute $C_P$,
exponentiating XQ to compute $C_Q$,
merging $C_P$ and $C_Q$ to compute C, wherein C is a 1024-bit number, and
retrieving C from the session memory;
wherein the method further comprises (a) selecting one of a plurality of session controllers; (b) setting the busy bit for the one session controller; and (c) clearing the busy bit for the one session controller.

20. The method of claim 19, further comprising:
selecting two session controllers of 32 available session controllers;
setting the busy bits for the two session controllers
wherein loading argument X into session memory includes:
loading part of the argument X into the session memory of one of the two session controllers;
loading the remainder of the argument X into the session memory of the other of the two session controllers;
wherein the argument X is a 2048-bit number;
wherein C is a 2048-bit number; and
clearing the busy bits for the two session controllers.

21. The method of claim 19, further comprising:
selecting four session controllers of 32 available session controllers;
setting the busy bits for the four session controllers
wherein loading argument X into session memory includes:
loading a first part of the argument X into the session memory of a first of the four session controllers;
loading a second part of the argument X into the session memory of a second of the four session controllers;
loading a third part of the argument X into the session memory of a third of the four session controllers;
loading the remaining of the argument X into the session memory of a fourth of the four session controllers;
wherein the argument X is a 4096-bit number;
wherein C is a 4096-bit number; and
clearing the busy bits for the four session controllers.

22. The method of claim 19,
wherein the cleaving X mod P comprises:
setting A[513:0]=X[1023:510];
calculating Z[1026:0]=A[513:0]×μP[512:0], wherein μP[512]=1;
setting B[513:0]=Z[1026:512];
setting C[513:0]=X[513:0];
calculating Y[1025:0]=B[513:0]×P[511:0];
setting D[513:0]=Y[513:0];
calculating E[513:0]=C[513:0]−D[513:0];
if E>P then calculating E=E−P;
if E>P then E =E−P; and
setting $X_P$=E[511:0] as the result of the cleaving X mod P, whereby $X_P$ equals X mod P; and
wherein the cleaving X mod Q comprises:
setting A[513:0]=X[1023:510];
calculating Z[1026:0]=A[513:0]×μQ[512:0], wherein μQ[512]=1;
setting B[513:0]=Z[1026:512];
setting C[513:0]=X[513:0];
calculating Y[1025:0]=B[513:0]×Q[511:0];
setting D[513:0]=Y[513:0];
calculating E[513:0]=C[513:0]−D[513:0];
if E>Q then calculating E=E−Q;
if E>Q then E=E−Q; and
setting $X_Q$=E[511:0] as the result of the cleaving X mod Q, whereby $X_Q$ equals X mod Q.

23. The method of claim 19, wherein merging $C_P$ and $C_Q$ to compute C comprises:
if $C_P$>P then calculating $C_P$=$C_P$−P;
if $C_Q$>Q then calculating $C_Q$=$C_Q$−Q;
calculating A[512:0]=$C_Q$[511:0]−$C_P$[511:0];
if A<0 then calculating A[511:0]=A[511:0]+Q[511:0];
calculating B[1023:0]=A[511:0]×$P^{-1}$[511:0];
calculating D[511:0]=Cleave B[1023:0] mod Q[511:0], wherein μQ[512]=1;
calculating E[1023:0]=D[511:0]×P[511:0];
calculating C[1023:0]=E[1023:0]+Cp[511:0]; and
wherein C[1023:0] is the result of merging $C_P$ and $C_Q$.

24. The method of claim 19, wherein X is data which is to be encrypted.

25. The method of claim 19, wherein X is data which is to be decrypted.

26. The method of claim 19, wherein the session controller selected is one 32 available session controllers.

27. A device for performing computations, comprising:
a plurality of exponentiators; and
a chaining controller adapted to arrange a first group of said exponentiators into a first computational chain when the device is required to process exponentiations of a first size, and being further adapted to arrange a second group of said exponentiators into a second computational chain when the device is required to process exponentiations of a second size distinct from said first size;
wherein the memories of said plurality of exponentiators map into a single global address.

28. The device of claim 27, wherein said plurality of exponentiators operate independently when the device is required to process exponentiations of a third size distinct from said first and second sizes.

29. The device of claim 27, wherein said third size is 1K.

30. The device of claim 27, wherein said first size is 4K.

31. The device of claim 27, wherein said second size is 2K.

32. The device of claim 27, wherein the first and second groups are mutually exclusive.

33. The device of claim 27, wherein said device is adapted to perform RSA exponentiations.

34. The device of claim 27, wherein each of said plurality of exponentiators is adapted to simultaneously process eight 1K exponentiations, four 2K exponentiations, or two 8K exponentiations.

35. The device of claim 27, wherein said chaining controller is a direct memory access controller which is adapted to load arguments and control information into the internal memory and registers of said plurality of exponentiators.

36. The device of claim 35, wherein said chaining controller is further adapted to retrieve exponentiation results from the memory of said plurality of exponentiators.

37. The device of claim 35, wherein said chaining controller is further adapted to retrieve exponentiation results from the memory of said plurality of exponentiators via a single burst-capable thirty-two bit bus interface.

38. The device of claim 35, wherein each of said plurality of exponentiators comprises a plurality of session controllers, and wherein each of said plurality of session controllers is adapted to process separate exponentiations concurrently.

39. The device of claim 38, wherein each of said plurality of exponentiators comprises a single set of computation hardware shared between the plurality of session controllers in a pipelined manner.

40. The device of claim 27, wherein each of said plurality of exponentiators is independently connected to said chaining controller.

41. A device for performing computations, comprising:
a plurality of exponentiators, wherein each of said plurality of exponentiators is adapted to simultaneously process eight 1K exponentiations, four 2K exponentiations, or two 8K exponentiations; and
a chaining controller adapted to arrange a first group of said exponentiators into a first computational chain when the device is required to process exponentiations of a first size, and being further adapted to arrange a second group of said exponentiators into a second computational chain when the device is required to process exponentiations of a second size distinct from said first size.

42. A device for performing computations, comprising:
a plurality of exponentiators; and
a chaining controller adapted to arrange a first group of said exponentiators into a first computational chain when the device is required to process exponentiations of a first size, and being further adapted to arrange a second group of said exponentiators into a second computational chain when the device is required to process exponentiations of a second size distinct from said first size;
wherein said chaining controller is a direct memory access controller which is adapted to load arguments and control information into the internal memory and registers of said plurality of exponentiators, wherein each of said plurality of exponentiators comprises a plurality of session controllers, and wherein each of said plurality of session controllers is adapted to process separate exponentiations concurrently.

* * * * *

UNITED STATES PATENT AND TRADEMARK OFFICE
CERTIFICATE OF CORRECTION

PATENT NO. : 7,233,970 B2  
APPLICATION NO. : 10/078252  
DATED : June 19, 2007  
INVENTOR(S) : Greg North et al.

Page 1 of 1

It is certified that error appears in the above-identified patent and that said Letters Patent is hereby corrected as shown below:

On the cover sheet, (73) Assignee, please delete "Cipher Corporation Limited" and insert therefore -- nCipher Corporation Limited --.

Signed and Sealed this

Eighteenth Day of March, 2008

JON W. DUDAS  
*Director of the United States Patent and Trademark Office*